(12) United States Patent
Muldowney et al.

(10) Patent No.: US 11,786,389 B2
(45) Date of Patent: Oct. 17, 2023

(54) SWEAT PAD AND METHODS OF USING SAME

(71) Applicant: Hemispheres for All, LLC, Byron, IL (US)

(72) Inventors: Thomas A. Muldowney, Byron, IL (US); Karl R. Schmitt, Byron, IL (US)

(73) Assignee: Hemispheres for All, LLC, Byron, IL (US)

( * ) Notice: Subject to any disclaimer, the term of this patent is extended or adjusted under 35 U.S.C. 154(b) by 1 day.

(21) Appl. No.: 17/688,876

(22) Filed: Mar. 7, 2022

(65) Prior Publication Data

US 2022/0192855 A1 Jun. 23, 2022

Related U.S. Application Data

(60) Continuation of application No. 16/986,266, filed on Aug. 6, 2020, now Pat. No. 11,298,254, which is a
(Continued)

(51) Int. Cl.
*A61F 5/00* (2006.01)
*A61F 13/40* (2006.01)
*A61M 35/00* (2006.01)

(52) U.S. Cl.
CPC ........... *A61F 5/0093* (2013.01); *A61M 35/00* (2013.01); *A61M 35/006* (2013.01);
(Continued)

(58) Field of Classification Search
CPC .......... A61F 5/0093; A61F 5/451; A61F 5/44; A61F 5/4401; A61F 5/4404; A61F 5/442; A61F 5/443; A61F 2005/4402; A61F 13/47; A61F 13/14; A61F 13/4702; A61F 13/4704; A61F 13/47218; A61F 13/47272; A61F 13/4752; A61F 13/4753; A61F 13/4755; A61F 13/4756; A61F 13/47236; A61F 13/47245; A61F 13/15; A61F 13/00004; A61F 13/204; A61F 13/2071; A61F 2013/4706; A61F 2013/4708; A61F 2013/2011; A61F 2013/15113; A61F 2013/1513; A61F 2013/00327; A61F 2013/15121; A61F 2013/15292; A61F 2013/00102; A61F 2013/00319; A61F 2013/15219; A61F 2/0004; A61F 2/0009;
(Continued)

(56) References Cited

U.S. PATENT DOCUMENTS 44,744 A 10/1864 Pease
3,211,145 A 10/1965 Rosenthal
(Continued)

FOREIGN PATENT DOCUMENTS

CN 1666727 A 9/2005
EP 0692263 A2 1/1996
(Continued)

*Primary Examiner* — Tarla R Patel
(74) *Attorney, Agent, or Firm* — Incubate IP; Randy R. Micheletti

(57) ABSTRACT

The present disclosure provides devices for preventing or absorbing fluid (e.g., sweat) and/or odors from the intergluteal cleft of a subject. In some embodiments, the present disclosure provides devices for treating or preventing hemorrhoids and methods of using same.

16 Claims, 14 Drawing Sheets

Related U.S. Application Data division of application No. 14/970,831, filed on Dec. 16, 2015, now abandoned.

(52) U.S. Cl.
CPC . *A61M 2202/04* (2013.01); *A61M 2205/6018* (2013.01); *A61M 2210/1067* (2013.01)

(58) Field of Classification Search
CPC ...... A61F 5/30; A61F 5/32; A61F 5/34; A61F 5/00; A61F 13/00; A61F 13/00008; A61F 13/00012; A61F 13/00017; A61F 13/00021; A61F 13/00025; A61F 13/04; A61F 13/06; A61F 13/063; A61F 13/474; A61F 13/475; A61F 13/471; A61F 13/472; A61F 13/47209; A61F 13/4751; A61F 13/4757; A61F 13/4758; A61F 2013/00089; A61F 2013/00093; A61F 2013/00097; A61F 2013/00119; A61F 2013/00127; A61F 2013/00272; A61F 2013/00314; A61F 2013/00361; A61F 2013/00544; A61F 2013/00548; A61F 2013/00574; A61F 2013/00578; A61F 2013/00697; A61F 2013/00702; A61F 2013/15569

See application file for complete search history.

(56) References Cited

U.S. PATENT DOCUMENTS

| | | |
|---|---|---|
| 4,702,237 A | 10/1987 | Gianopoulos |
| 5,228,853 A | 7/1993 | Wojtowski |
| 5,695,484 A | 12/1997 | Cox |
| 6,311,332 B1 | 11/2001 | Lien |
| 6,554,813 B2 | 4/2003 | Kolby-Falk |
| 6,913,573 B1 | 7/2005 | Viscomi |
| 7,429,689 B2 | 9/2008 | Chen et al. |
| 7,530,973 B2 | 5/2009 | Tanio |
| 8,062,277 B2 | 11/2011 | Fleming |
| D666,296 S | 8/2012 | Sibhatu |
| 8,252,335 B2 | 8/2012 | Maraccini |
| 8,419,699 B2 | 8/2013 | Giloh |
| 8,591,488 B2 | 11/2013 | Brezoczky et al. |
| 8,821,466 B2 | 9/2014 | Brezoczky et al. |
| D720,848 S | 1/2015 | Brezoczky |
| D721,170 S | 1/2015 | Brezoczky |
| 8,979,814 B2 | 3/2015 | Brezoczky et al. |
| 9,095,476 B2 | 8/2015 | Brezoczky et al. |
| D750,226 S | 2/2016 | Brezoczky |
| 9,278,034 B2 | 5/2016 | Brezoczky et al. |
| D768,294 S | 10/2016 | Brezockzy |
| 9,750,648 B2 | 9/2017 | Brezoczky et al. |
| D914,205 S | 3/2021 | Muldowney |
| D930,155 S | 9/2021 | Muldowney |
| 11,298,254 B2 * | 4/2022 | Muldowney .......... A61F 5/0093 |
| 2001/0003157 A1 | 6/2001 | Toth |
| 2002/0040211 A1 | 4/2002 | Drevik |
| 2002/0193766 A1 | 12/2002 | Gell |
| 2004/0162537 A1 | 8/2004 | Manasek |
| 2004/0167479 A1 | 8/2004 | Warren |
| 2007/0260163 A1 | 11/2007 | Blurton |
| 2010/0030189 A1 | 2/2010 | Fleming |
| 2013/0035656 A1 | 2/2013 | Moriya |
| 2013/0197459 A1 | 8/2013 | Brezoczky et al. |
| 2014/0121624 A1 | 5/2014 | Kirby et al. |
| 2015/0216699 A1 | 8/2015 | Kobke |
| 2016/0022511 A1 | 1/2016 | Brezoczky et al. |

FOREIGN PATENT DOCUMENTS

| | | |
|---|---|---|
| EP | 2811960 B1 | 6/2017 |
| WO | 2007073246 A1 | 6/2007 |
| WO | 2013116391 A2 | 8/2013 |

* cited by examiner

SWEAT PAD AND METHODS OF USING SAME

CROSS-REFERENCE TO RELATED APPLICATIONS

This application is a continuation of U.S. patent application Ser. No. 16/986,266 filed on Aug. 6, 2020, entitled "SWEAT PAD AND METHODS OF USING SAME," and issued on Apr. 12, 2022, as U.S. Pat. No. 11,298,254, which is a divisional of U.S. patent application Ser. No. 14/970,831, filed on Dec. 16, 2015 and entitled "SWEAT PAD AND METHODS OF USING SAME," each of which is incorporated herein by reference and relied upon.

TECHNICAL FIELD

The present disclosure relates to devices for absorbing a bodily fluid (e.g., sweat), relieving pain and/or itching, and/or relieving one or more symptoms of hemorrhoids.

BACKGROUND

Sweating and itching around the anus is a common occurrence, and can be embarrassing to those who suffer from it and its other symptoms. Hemorrhoids are also common, and often impart itching, pain, swelling and bleeding. Other conditions, such as proximal decubitus ulcers, also include symptoms emanating from the anal or perianal regions. Surgical interventions are associated with increased risks of infection and other complications. In addition, some conditions (e.g., early stage hemorrhoids) are not indicated for surgical correction, yet are associated with extreme discomfort for many subjects. A need exists for non-surgical treatments for these and other similar conditions.

SUMMARY

The present disclosure provides devices for absorbing a bodily fluid (e.g., sweat), relieving pain and/or itching, and/or relieving one or more symptoms of hemorrhoids. In some embodiments, the device is placed adjacent to (e.g., in contact with) an existing hemorrhoid, or adjacent to (e.g., in contact with) a location of a subject where a hemorrhoid is likely to form. In some embodiments, the device absorbs fluid (e.g., sweat) when placed adjacent to (e.g., in contact with) skin of a subject.

In some embodiments, the present disclosure provides an absorbent device comprising a first layer including a body-facing surface containing an anti-stick material; a second layer disposed opposite the first body-facing surface; and a third layer disposed between the first and second layers and comprising an absorbent material, wherein at least a portion of the first layer includes a contour that substantially deviates from a plane.

In other embodiments, the present disclosure provides an absorbent device comprising a first, body-facing layer comprising a plurality of dimples; a second layer disposed opposite the first layer; and an inner core disposed between the first, body-facing layer and the second layer.

In some embodiments, the present disclosure provides methods of treating or preventing a hemorrhoid in a subject, the method comprising placing a device as disclosed herein at least partially within an intergluteal cleft of a subject.

In some embodiments, the present disclosure provides methods of absorbing a fluid proximal to an anus of a subject, the method comprising placing a device as disclosed herein at least partially within an intergluteal cleft of a subject.

In some embodiments, the present disclosure provides methods of reducing or eliminating itching proximal to an anus of a subject, the method comprising placing a device as disclosed herein at least partially within an intergluteal cleft of a subject.

These and other embodiments are described in greater detail below.

DETAILED DESCRIPTION

Certain specific details are set forth in the following description and in FIGS. 1A-13D to provide a thorough understanding of various embodiments of the technology. For example, several embodiments of devices for treating or preventing hemorrhoids are described in detail below. The present technology, however, may be used in conjunction with other therapies, such as a surgical procedure, topical application of medicaments, and the like. Other details describing well-known structures and systems often associated with devices for application to skin or adjacent to skin have not been set forth in the following disclosure to avoid unnecessarily obscuring the description of the various embodiments of the technology. A person of ordinary skill in the art, therefore, will accordingly understand that the technology may have other embodiments with additional elements, or the technology may have other embodiments without several of the features shown and described below with reference to FIGS. 1A-13D.

1. Selected Embodiments of Devices for Absorbing Fluid from Skin of a Subject

Generally, devices of the present disclosure absorb fluid (e.g., sweat) from skin of a subject. In some embodiments, the skin includes skin proximal to the subject's anus (e.g., at least in part in the subject's intergluteal cleft). Accordingly, in some embodiments, devices according to the present disclosure are configured to be placed, at least in part, in a subject's intergluteal cleft (e.g., proximal to the subject's anus such as perianal tissue). In some embodiments, the fluid includes blood, sweat, feces, urine and/or pus.

In some embodiments, a device according to the present disclosure is sized such that the portion most proximal to the subject's anus (e.g., a portion that is in contact with perianal skin) is proportional to the subject's size (e.g., the subject's height, weight, BMI, waist circumference, etc.).

Figure 1A:
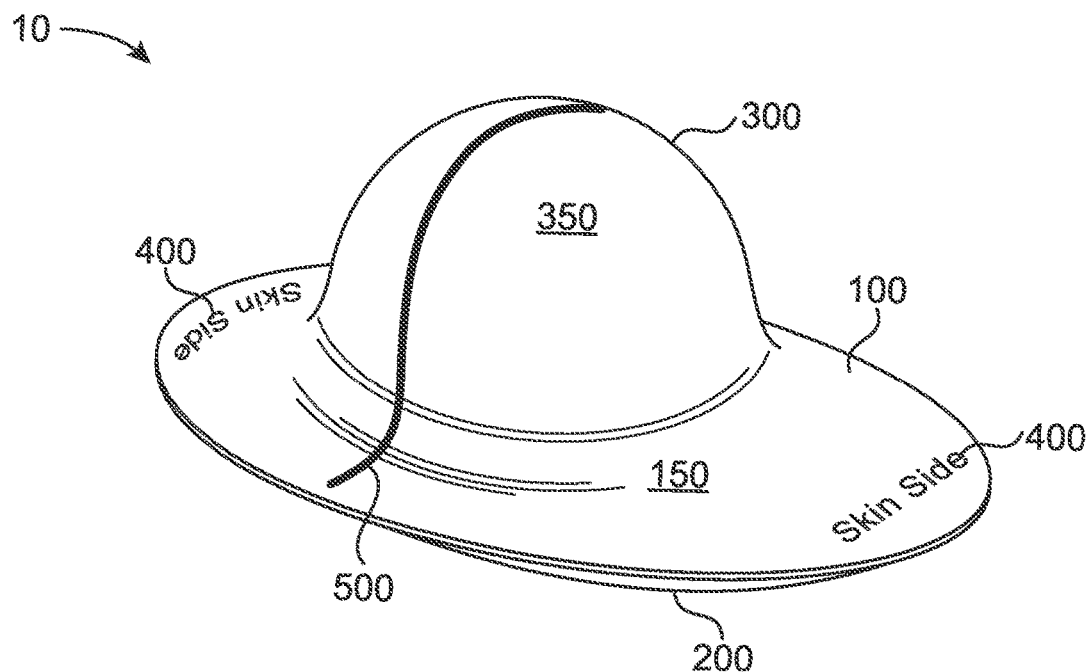
FIG. 1A shows a perspective view of the top side of one embodiment of a device according to the present technology.
Figure 1B:
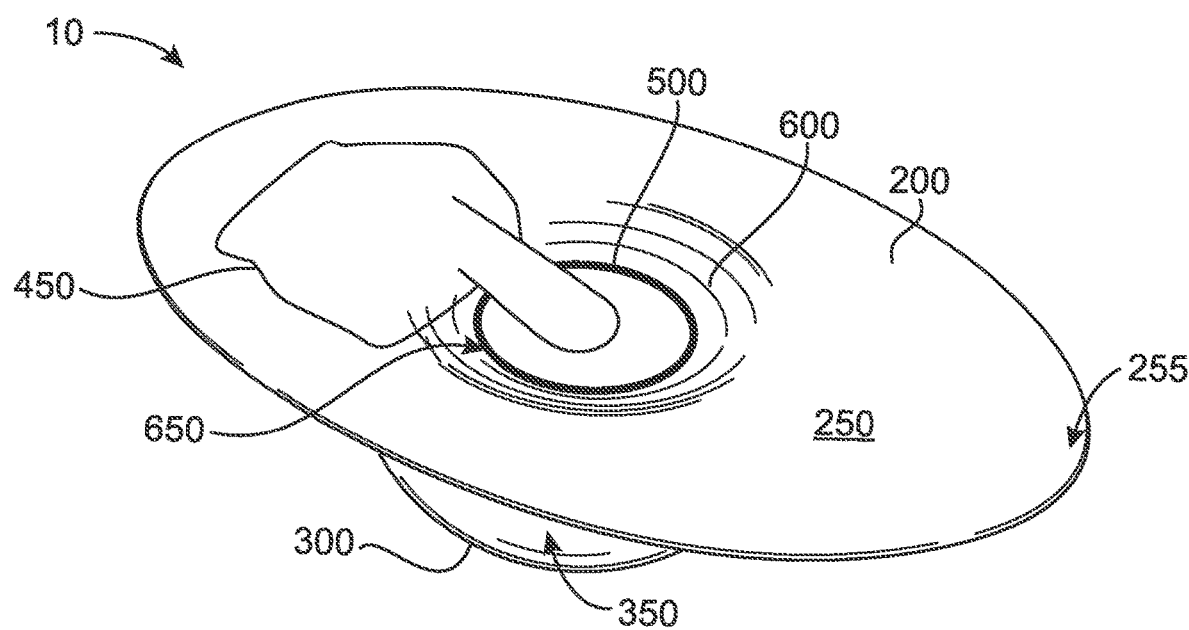
FIG. 1B shows a perspective view of the bottom side of the device of FIG. 1A.
Figure 2:
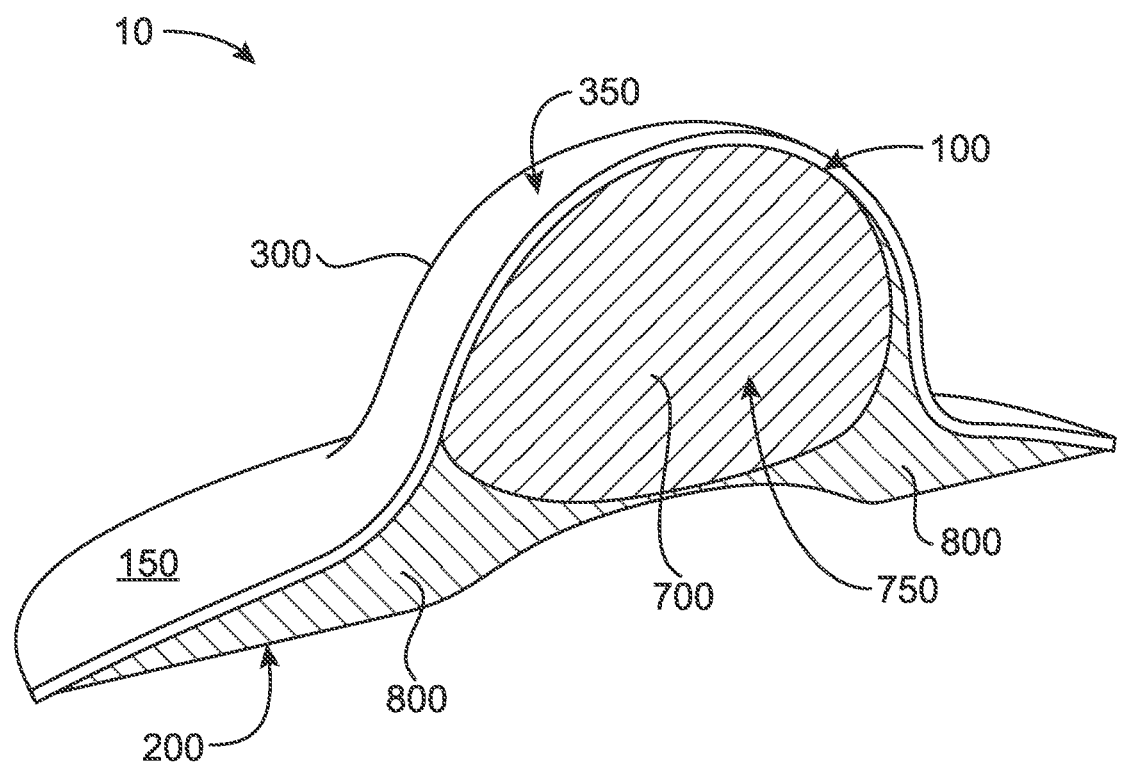
FIG. 2 shows a perspective and cross-sectional view of the device of FIGS. 1A and 1B.

Referring now specifically to FIGS. 1A-1B and 2, a device 10 according to one embodiment of the present disclosure comprises a first layer 100 and a second layer 200 disposed opposite the first layer 100. At least a portion of the first layer 100 includes a contour 300 that deviates from a plane (e.g., from a flat planar surface).

The first layer 100 is oriented on the device 10 to be on contact with or adjacent to the subject. The first layer 100 may be formed of any material suitable for direct contact with skin and allows moisture to penetrate through the first layer 100. In some embodiments, the first layer 100 comprises cotton. The first layer 100 includes a surface (e.g., a body-facing surface) 150. The surface 150 may include a coating, such as a waxy coating, to prevent the first layer 100 from adhering to the subject's skin too strongly. In some embodiments, the surface 150 includes a texture. In some embodiments, the texture increases the adherence of the device 10 to the skin of the subject. In some embodiments, the texture includes one or more dimples.

In some embodiments, the first layer 100 further includes one or more informational markings 400 for providing information to the subject. For example, the informational markings 400 may indicate which side of the device 10 should be in contact with the subject's skin.

In some embodiments, the first layer 100 further includes one or more orientation markings 500 for indicating to the subject how the device 10 should be oriented upon application. For example, as shown in FIG. 1A, the orientation markings 500 may include a line indicating the midline of the device 10 which should be aligned parallel to the intergluteal cleft.

The contour portion 300 of the first layer 100 deviates from a plane (e.g., from a flat planar surface) with respect to the remaining portions of the first layer 100. For example, as shown in FIG. 1A, the contour portion 300 substantially protrudes from the first layer 100. In some embodiments, such as that shown in FIG. 1A, the contour portion 300 protrudes from the first layer 100 to form a generally spheroid shape. In other embodiments, the contour portion 300 forms a different shape, such as a disc, a mound, a cone, a teardrop, or a combination thereof. In other embodiments, the contour portion 300 substantially recedes from the first layer 100, for example to form a dent or divot in the first layer 100. The contour portion 300 includes a surface 350 that may optionally include a texture similar to that described with respect to surface 150 of the first layer 100. In other embodiments, the surface 350 does not include a texture, even in embodiments where surface 150 includes a texture. In some embodiments, the contour portion 300 is sized proportional to the subject's size (e.g., the subject's height, weight, BMI, waist circumference, etc.).

The second layer 200 of the device 10 may be formed of any durable material, optionally suitable for direct contact with skin, and which may allow the fluid to penetrate through the second layer 200. In some embodiments, the second layer 200 comprises cotton. As shown in FIG. 1B, the second layer 200 of the device 10 includes a second surface 250 which, in some embodiments, may include a coating (e.g., a waxy coating) to improve the integrity of the second layer 200 to mechanical- or fluid-driven degradation. In some embodiments, the second surface 250 includes a texture. In some embodiments, the texture increases the adherence of the device 10 to the skin of the subject, for example to improve handling and manipulation of the device 10 during application. In some embodiments, the texture includes one or more dimples.

The second layer 200 may include a second contour portion 600 which, in some embodiments, includes a contour that substantially deviates from a plane (e.g., from a planar surface defined at least in part by the remainder of the second layer 200). For example, as shown in FIG. 1B, the second contour portion 600 may recede from a planar surface defined by the remainder of the second layer 200 such that an indentation is formed in the second layer 200. The second contour portion 600 includes a surface 650 that may optionally include a texture, such as one or more dimples, to improve handling and manipulation of the device 10 during application.

In some embodiments, the second layer 200 further includes one or more informational markings 450 for providing information to the subject. For example, the informational markings 450 may indicate where the subject might apply pressure to properly install the device 10 in an intergluteal cleft.

In some embodiments, the second layer 200 further includes one or more graphical indicators 550 for indicating to the subject how the device 10 should be oriented upon application. For example, as shown in FIG. 1B, the orientation markings 550 may indicate a central zone indicating the center of the device 10, which should ideally be aligned with the anus of the subject upon application.

The first layer 100 and the second layer 200 may be secured to each other around the periphery by any suitable means known to those of skill in the art. In one embodiment, shown in FIG. 1B, the first layer 100 and the second layer 200 are joined together by a seam or seal 255. In some embodiments, for example when the first layer 100 and/or the second layer 200 comprise cotton, the seam or seal 255 may be a physical joint (e.g., a sewn seam) or a chemical joint (e.g., an adhesive-enabled seal). In some embodiments, the first layer 100 and the second layer 200 are joined together by heat and/or compression.

In some embodiments, the device 10 includes a cross-sectional shape defined by the first layer 100, the second layer 200 and the contour 300. The cross-sectional shape may be chosen to enhance ease of use (e.g., installation and/or removal) of the device 10, subjects' comfort, etc. In some embodiments, the cross-sectional shape is substantially round, ovoid, rod-shaped, or polygonal. For example and without limitation, the cross-sectional shape may include a circle, an oval, a rod, a rectangle, a square, a trapezoid, a rhombus, a parallelogram, a triangle, a hexagon, a pentagon, a heptagon, an octagon, a nonagon, a squircle, a portion of any of the forgoing (e.g., a semi-circle), a tapered configuration of any of the foregoing, or a combination of two or more of any of the foregoing (e.g., a cross-sectional profile including a quadrilateral portion and one or more protruding finger-like portion from one of the quadrilateral lengths and/or corners).

As shown in FIG. 2, the embodiment of FIGS. 1A-1B includes a third layer 700 disposed between the first layer 100 and the second layer 200. The third layer 700 includes a filler material 750 for absorbing fluids and/or delivering an active agent to the subject upon application of the device 10 in the subject's intergluteal cleft. In some embodiments, the third layer 700 occupies the entire space between the first layer 100 and the second layer 200. In other embodiments, such as the one shown in FIG. 2, the filler material 750 comprises only a portion of the third layer 700 (e.g., occupies only a portion of the space between the first layer 100 and the second layer 200). In such embodiments, the remainder of the space between the first layer 100 and the second layer 200 not occupied by the filler material 750 may comprise a second filler material 800, which may be a relatively firm, structurally supportive material like cotton or a foam, for securing the filler material 750 in a desired location within the device 10. For example, as shown in FIG. 2, the third layer 700 may comprise an absorbent material 750 such as cotton, located substantially within the non-planar contour portion 300 of the first layer 100. To ensure the absorbent material 750 remains substantially in that location within the device 10, the third layer 700 further includes a second filler material 800 which is significantly more rigid than the absorbent material 750. In use, the more rigid second filler material 800 substantially prevents the absorbent material 750 from being forced out of its original location within the device 10 by, for example, physical forces exerted by a subject's gluteal muscles on the device 10.

Figure 3A:
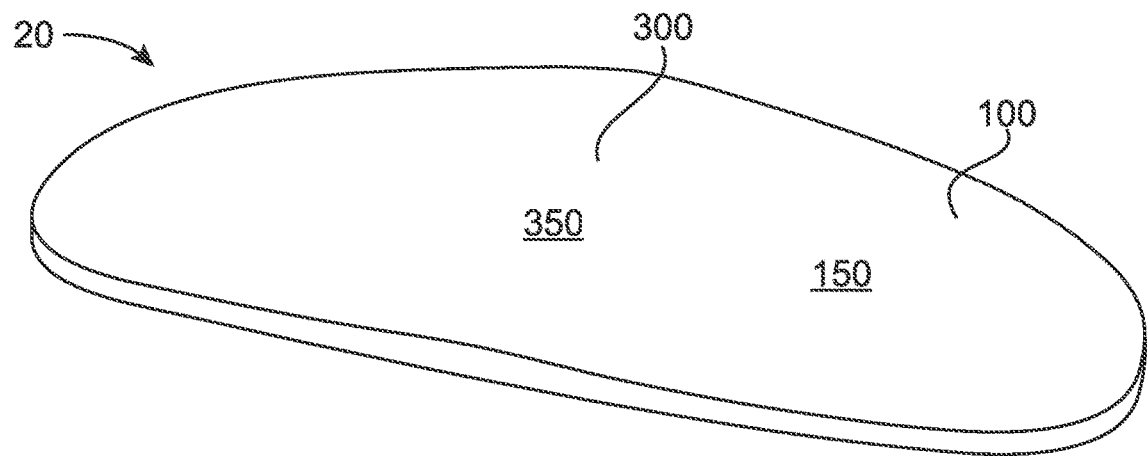
FIG. 3A shows a perspective view of another embodiment of a device according to the present technology.
Figure 3B:
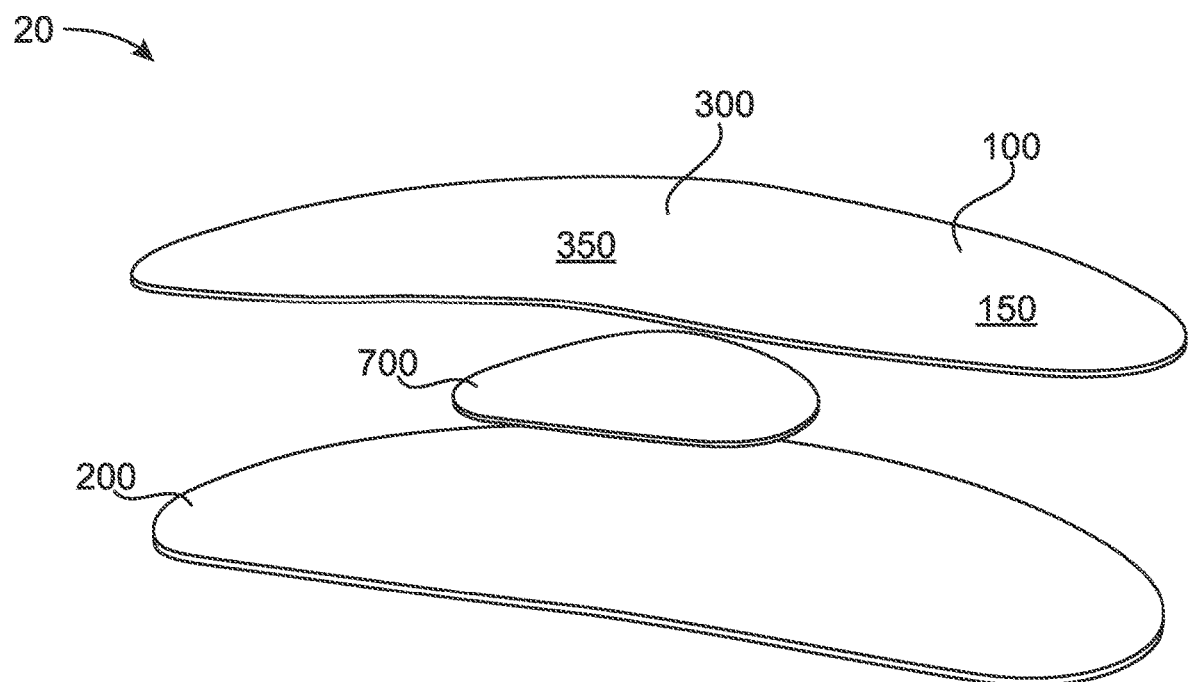
FIG. 3B shows an expanded perspective view of the device of FIG. 3A.

In another embodiment, shown in FIGS. 3A-3B, a device 20 according to the present disclosure comprises a first layer 100 and a second layer 200 disposed opposite the first layer 100. At least a portion of the first layer 100 includes a contour 300 that deviates from a plane (e.g., from a flat planar surface).

General features of the first layer 100, the second layer 200, and the third layer 700 are substantially as described above with respect to FIGS. 1A-2.

A third layer 700 is disposed between the first layer 100 and the second layer 200, substantially in alignment with the contour portion 300 of the first layer 100. In some embodiments, the contour portion 300 of the first layer 100 is formed at least in part by the presence of the third layer 700 between the first layer 100 and the second layer 200.

In some embodiments, such as that shown in FIGS. 3A-3B, the third layer 700 comprises a shape that is substantially discoid. For example, the third layer 700 may be a round or circular pouch containing an absorbent material (as described above with respect to FIGS. 1A-2) that is secured between the first layer 100 and the second layer 200, causing the contour portion 300 of the first layer 100 to adopt a substantially discoid shape.

Figure 4:
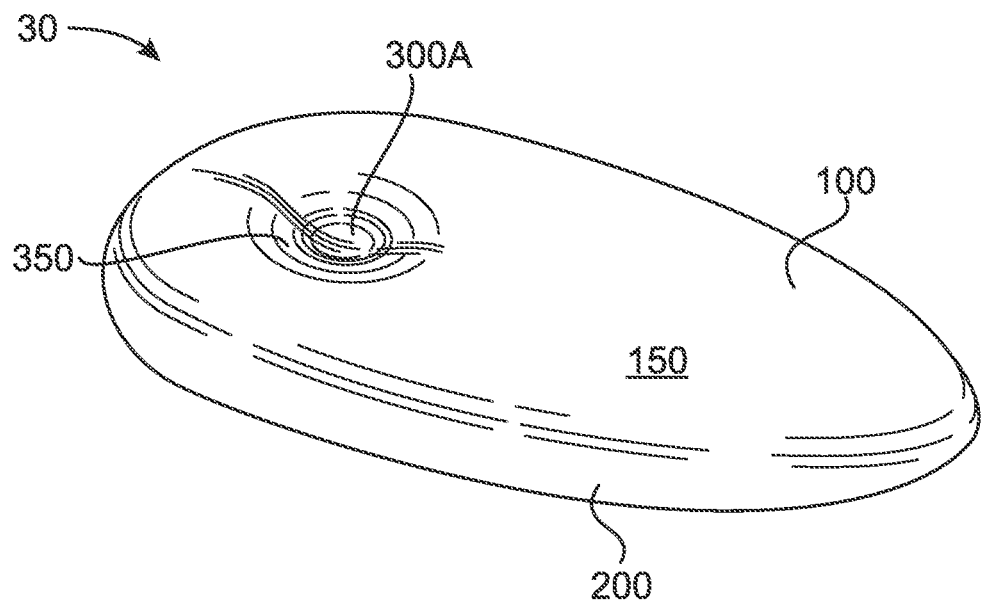
FIG. 4 shows a perspective view of another embodiment of a device according to the present technology.
Figure 5:
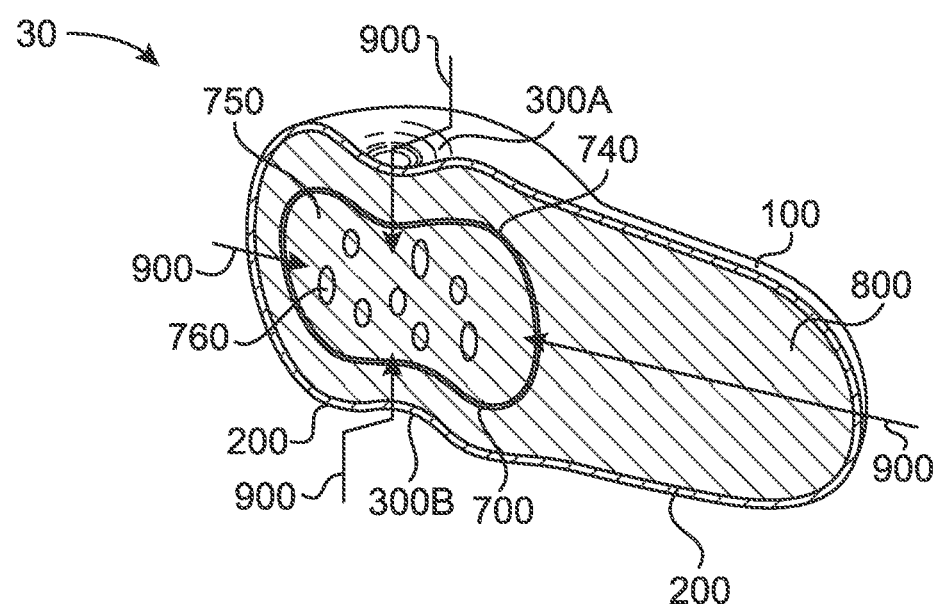
FIG. 5 shows a perspective and cross-sectional view representative of various embodiments of devices according to the present technology.

In another embodiment, shown in FIGS. 4-5, the first layer 100 and second layer 200 may be a continuous or semi-continuous form (e.g., without a flattened seam or seal 255 as shown in FIG. 1B) to form a device 30 having rounded edges. In such embodiments, the contour portion 300A may adopt any desired shape including, for example, a recessed cavity. The first layer 100, second layer 200, and/or the contour portion 300A may each include a surface 150, a surface 250 (not shown due to perspective) and/or a surface 350, respectively, as described above with respect to other embodiments. In some embodiments, the contour portion 300A is sized proportional to the subject's size (e.g., the subject's height, weight, BMI, waist circumference, etc.).

As shown in FIG. 5, the second layer 200 may include a contour portion 300B in addition to, or instead of, the contour portion 300A of the first layer 100. In embodiments including contour portions 300A/300B in both the first layer 100 and the second layer 200, respectively, the two contour portions 300A/300B may have an identical shape. In other embodiments (not shown), the two contour portions 300A/300B may have a substantially similar shape, or substantially different shapes. In some embodiments, the contour portion 300A/300B is sized proportional to the subject's size (e.g., the subject's height, weight, BMI, waist circumference, etc.).

The device 30 may include an inner core 700. Any remaining space between the first layer 100 and the second layer 200 may be filled with an absorbent filler material 800. In such embodiments, the absorbent filler material 800 acts to draw fluid into the device 30 through the first layer 100 and/or the second layer 200 and eventually to the inner core 700, for example along moisture paths 900.

In any embodiment disclosed herein, the inner core 700 (also referred to as the third layer 700 in various embodiments) may include a hygroscopic material 750, such as cotton or any other aqueous absorbent material or combination of materials. The inner core 700 may include an active agent 760. In some embodiments, the active agent 760 is a deodorant. In some embodiments, the active agent 760 is an antibacterial agent. In some embodiments, the active agent 760 is a hemorrhoid relief agent (e.g., disaccharide polysulfide). In some embodiments, the active agent 760 is a numbing agent (e.g., a topical anesthetic such as benzocaine, butamben, dibucaine, lidocaine, oxybuprocaine, pramoxine, proparacaine, proxymetacaine, and tetracaine (alternatively referred to as amethocaine). In some embodiments, the active agent is two or more or three or more of: a deodorant, an antibacterial agent, and a hemorrhoid relief agent. In some embodiments, the active agent comprises a deodorant, an antibacterial agent, a hemorrhoid relief agent and a numbing agent.

Figure 6:
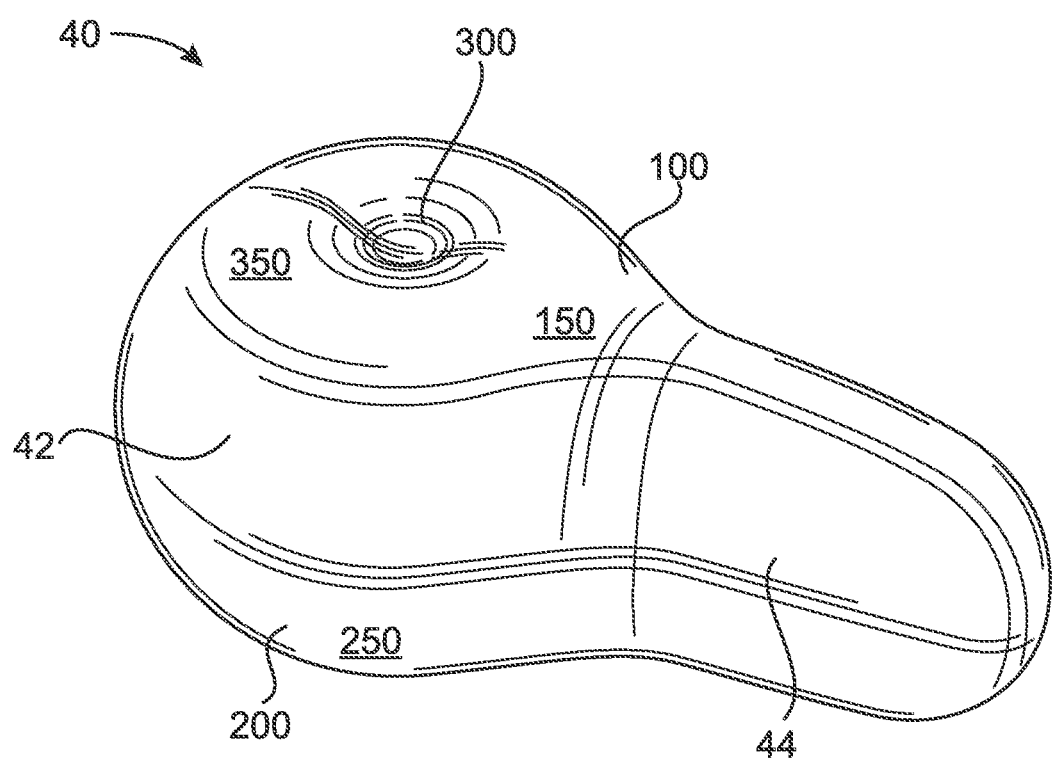
FIG. 6 shows a perspective view of another embodiment of a device according to the present technology.

In another embodiment, shown in FIG. 6, a device 40 according to the present disclosure comprises a substantially bulbous head portion 42 and a substantially narrow tail portion 44. In such embodiments, the tail portion 44 enables safe and efficient handling of the device 40, for example between a subject's thumb and forefinger, while remaining discreet after application within the subject's intergluteal cleft.

The device 40 may include a first layer 100, a second layer 200, and a contour portion 300, similar to those shown and described above with respect to FIGS. 1A-5. General features of the first layer 100, the second layer 200, and the contour portion 300, including surfaces 150, 250 and 350, are substantially as described above with respect to other illustrated embodiments.

Figure 7A:
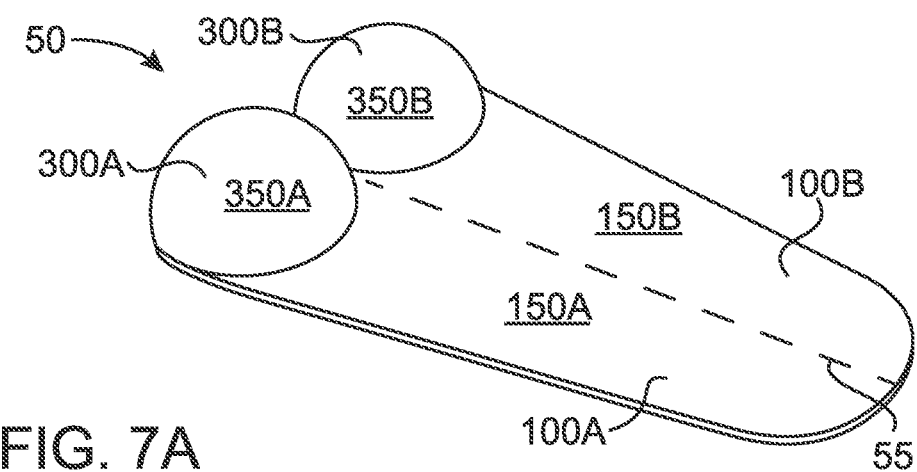
FIG. 7A shows a perspective view of another embodiment of a device according to the present technology.
Figure 7B:
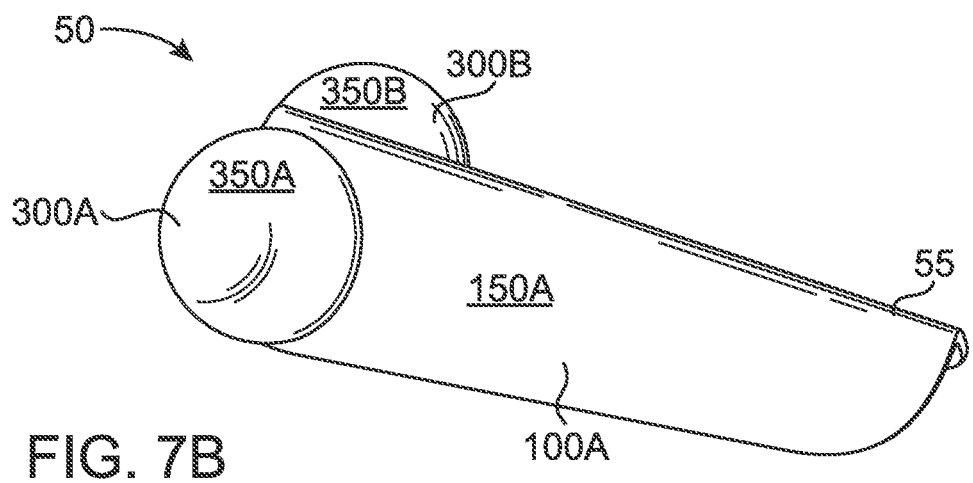
FIG. 7B shows a perspective view of the device of FIG. 7A part-way through being folded into a usable configuration.
Figure 7C:
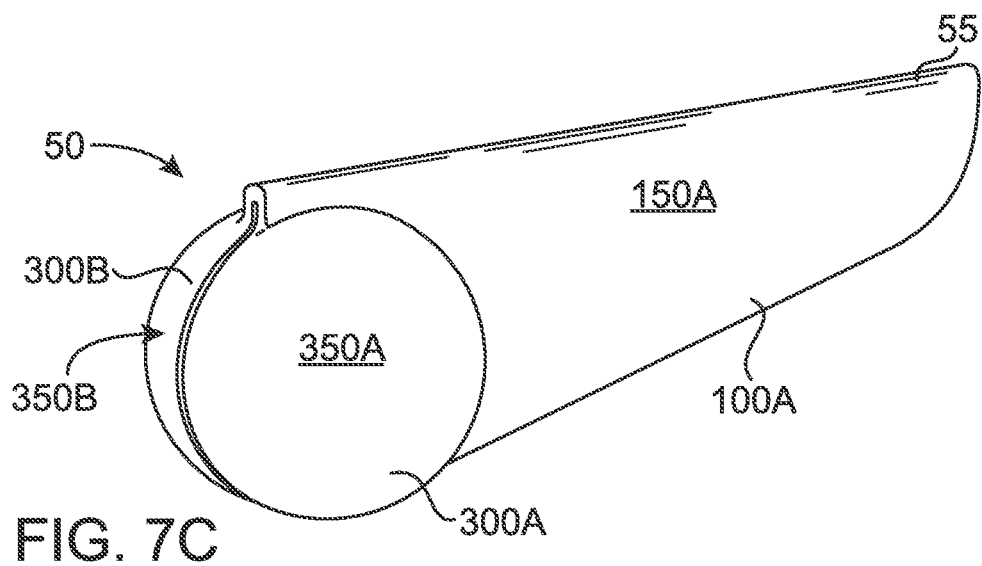
FIG. 7C shows a perspective view of the device of FIGS. 7A and 7B after being folded into a usable configuration.

As shown in FIGS. 7A-7C, another embodiment of a device 50 according to the present disclosure includes a foldable crease 55 along a length of the device 50 for enabling efficient packaging of the device 50. In such embodiments, the device 50 includes a bifurcated first layer 100A/100B comprising an absorbent material and an optional coating (e.g., a waxy coating) suitable for direct contact with skin. Each of the bifurcated first layers 100A and 100B may include a surface 150A/150B. The surfaces 150A/150B may have properties similar to those described above with respect to surface 150 in other embodiments.

The device 50 also includes a bifurcated contour portion 300A/300B which, after folding is complete (e.g., as shown in FIG. 7C), has properties substantially similar to contour portion 300 in other embodiments described herein. More specifically, each of contour portions 300A/300B may have a surface 350A/350B that includes a texture, such as a plurality of dimples. In some embodiments, the bifurcated contour portion 300A/300B, after the device 50 is folded as shown in FIG. 7C, is sized proportional to the subject's size (e.g., the subject's height, weight, BMI, waist circumference, etc.).

When ready for use, the subject folds the device 50 along foldable crease 55 until the contour portion 300A is in contact with and/or continuous with the contour portion 300B, according to a progression shown in FIG. 7A to FIG. 7B to FIG. 7C. The resulting folded device 50 (FIG. 7C) is then inserted within the intergluteal cleft such that the contour portion 300A/300B is in contact with the perianal tissue. When in position, the foldable crease 55 imparts a hinged outward force (e.g., a residual hinged spring force) which further enhances the stability of the device 50 in its installed position within the intergluteal cleft.

Figure 8:
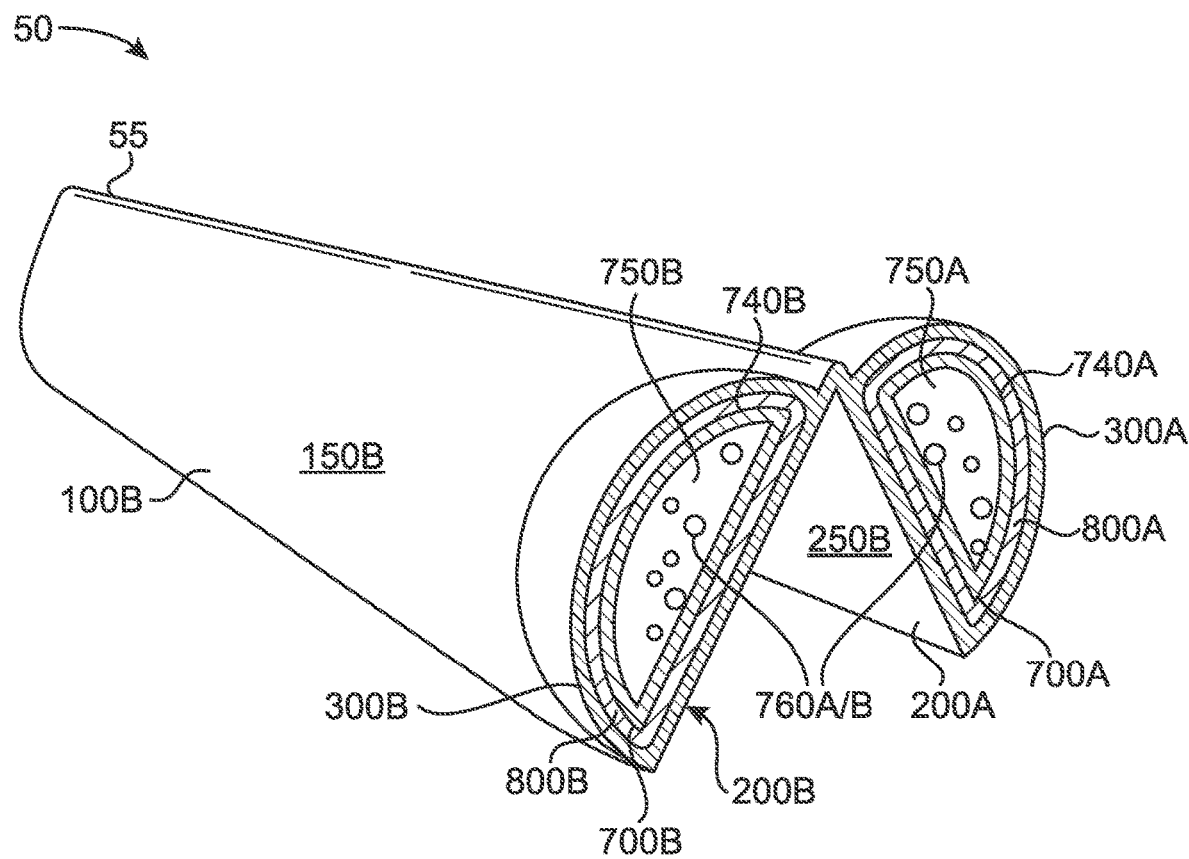
FIG. 8 shows a perspective and cross-sectional view of the device of FIGS. 7A-7C.

As shown in FIG. 8, the device 50 may include a bifurcated second layer 200A/200B disposed opposite the bifurcated first layer 100A/100B. The bifurcated second layer 200A/200B may be substantially the same as second layer 200 as described above with respect to other embodiments. For example, bifurcated second layer 200A may include a surface 250A, and bifurcated second layer 200B may include a surface 250B (not shown due to perspective) similar to or identical to second surface 250 described elsewhere in the present disclosure.

Similarly, the bifurcated contour portions 300A/300B may each include an inner core 700A/700B, which may each be substantially similar to inner core 700 described in connection with other embodiments disclosed herein. For example, inner core 700A/700B may include a hygroscopic material 750A/750B and optionally an active agent 760A/760B, all encapsulated in a permeable barrier layer 740A/740B. In some embodiments, an absorbent material 800A/800B is disposed between the permeable barrier layer 740A/740B and the first layer 100A/100B and optionally between the permeable barrier layer 740A/740B and the second layer 200A/200B.

An optional active agent 760A/760B may be included within the hygroscopic material 750A/750B. In some embodiments, active agent 760A is the same as the active agent 760B. In other embodiments, the active agent 760A is different than the active agent 760B.

Figure 9:
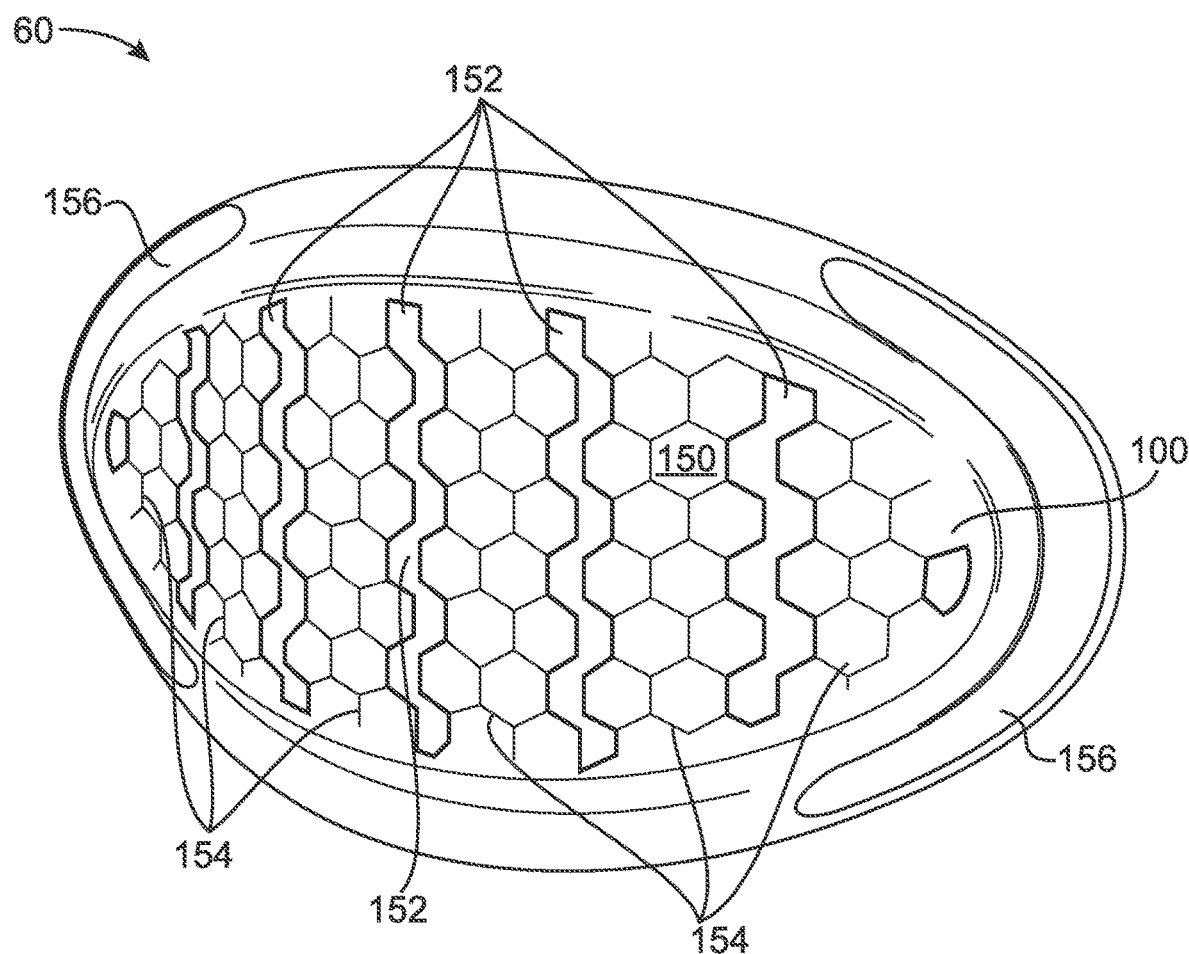
FIG. 9 shows a perspective view of another embodiment of a device according to the present technology.
Figure 10:
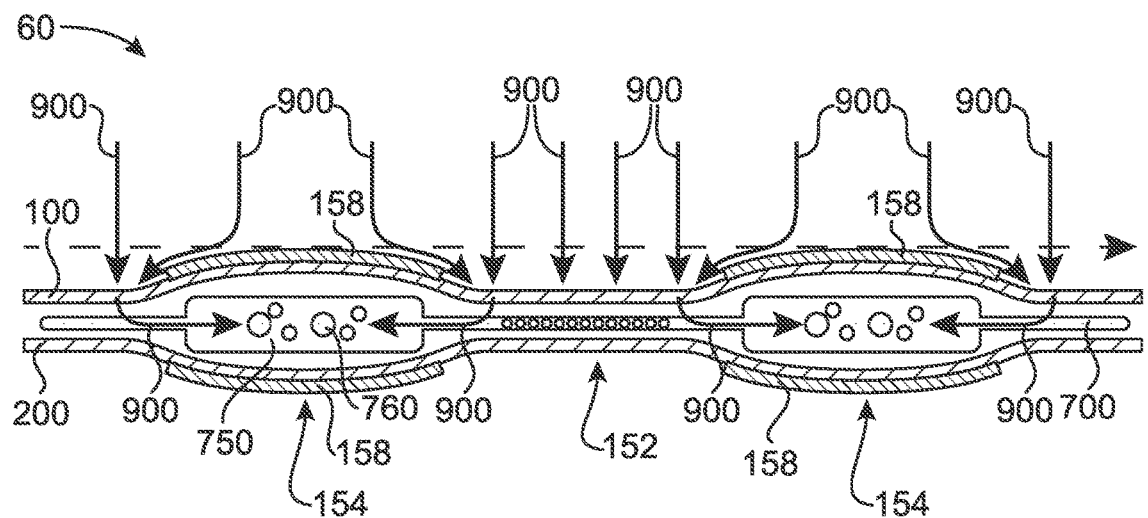
FIG. 10 shows a cross-sectional view of the device of FIG. 9.

In yet another embodiment, shown representatively in FIGS. 9-10, a device 60 according to the present disclosure comprises first layer 100 including a surface 150. The surface 150 includes at least one valley 152 and at least one plateau 154 for controlling flow of fluid into the device 60. In this embodiment, the device 60 also optionally includes a pair of adhesive areas 156 for providing additional adherence to the subject's skin upon application.

As shown in FIG. 10, the plateau portion(s) 154 may include a hydrophobic coating 158 which may attenuate the first layer 100 material's innate aqueous permeability properties. The valley(s) 152, in contrast, may not include the hydrophobic coating 158, enabling relatively easier permeability of fluids through the first layer 100 and/or the second layer 200 and into the third layer 700. In FIG. 10, this relative permeability difference between the plateau portions 154 and the valley portion(s) 152 is represented by moisture paths 900.

As in other embodiments, the third layer 700 may include a hygroscopic material 750 and optionally an active agent 760.

Figure 11:
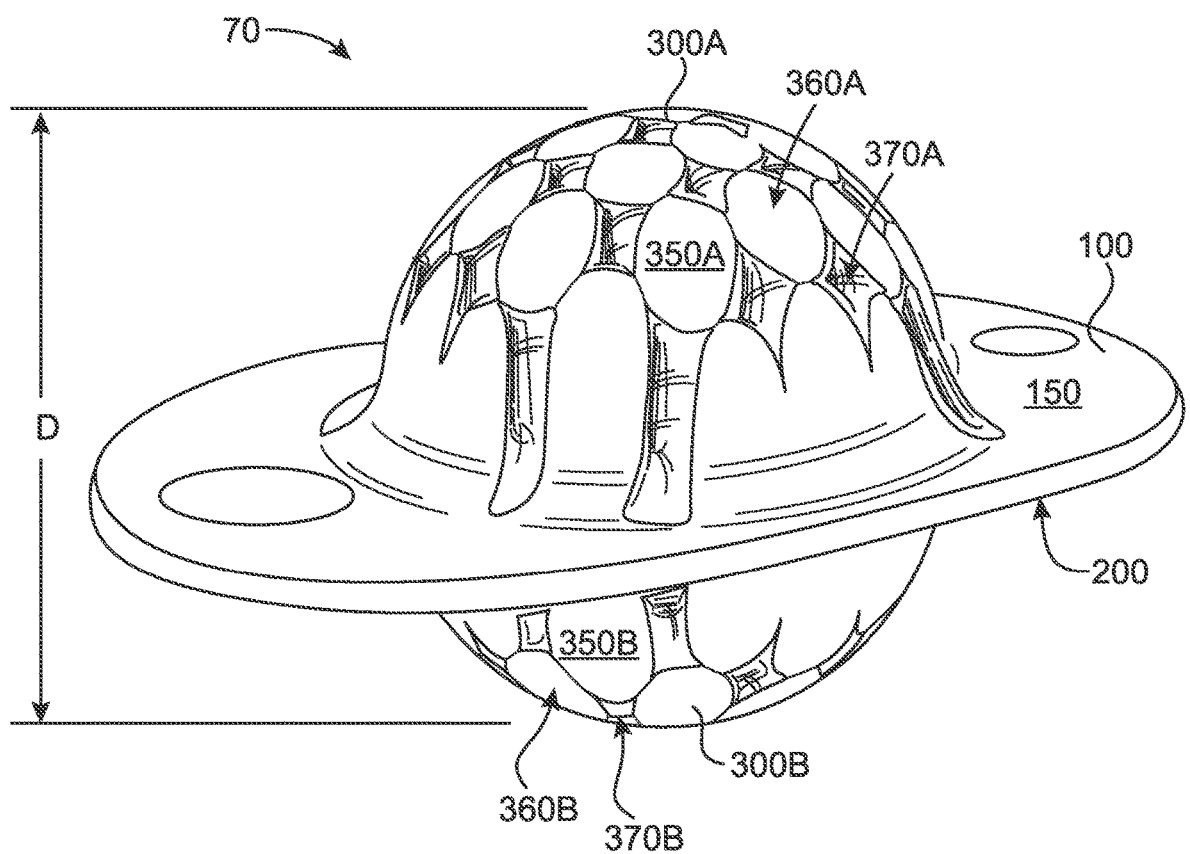
FIG. 11 shows a perspective view of another embodiment of a device according to the present technology.

In yet another embodiment, shown representatively in FIG. 11, a device 70 according to the present technology comprises a first layer 100 and a second layer 200 disposed opposite the first layer 100. Each of the first layer 100 and the second layer 200 may include a surface 150 and a surface 250, respectively, which may have properties similar to those described above in connection with other disclosed embodiments.

The first layer 100 includes a contour portion 300A, which may additionally include one or more pillars 360A and one or more cavities 370A between the pillars 360A. Fluid absorbed by the contour portion 300A may thus cause the pillars 360A to expand radially, and the cavities 370A to shrink accordingly.

The second layer 200 includes a contour portion 300B, which may additionally include one or more pillars 360B and one or more cavities 370B between the pillars 360B. Fluid absorbed by the contour portion 300B may thus cause the pillars 360B to expand radially, and the cavities 370B to shrink accordingly.

In such embodiments, the first layer 100 and the second layer 200, and especially contour portions 300A/300B, may absorb substantial amounts of fluid without substantially expanding (e.g., without a diameter D of the combined contour portions 300A/300B substantially increasing). In some embodiments, the contour portion 300A/300B is sized proportional to the subject's size (e.g., the subject's height, weight, BMI, waist circumference, etc.).

Referring now generally to FIGS. 12A-12F, the present disclosure provides another embodiment of a device 80 for absorbing a fluid from skin of a subject. In such embodiments, the device 80 is formed of a substantially uniform sheet of material. The device 80 comprises a top surface 8100 which includes a contour portion 8300. The top surface 8100 may be formed of any material suitable for direct contact with skin and allows moisture to penetrate into the device 80. In some embodiments, the top surface 8100 comprises cotton. The top surface 8100 includes a surface (e.g., a body-facing surface) 8150. The surface 8150 may include a coating, such as a waxy coating, to prevent the top surface 8100 from adhering to the subject's skin too strongly. In some embodiments, the surface 8150 includes a texture. In some embodiments, the texture increases the adherence of the device 80 to the skin of the subject. In some embodiments, the texture includes one or more dimples.

In some embodiments, the top surface 8100 further includes one or more informational markings 8400 for providing information to the subject. For example, the informational markings 8400 may indicate which side of the device 80 should be in contact with the subject's skin.

Figure 12A:
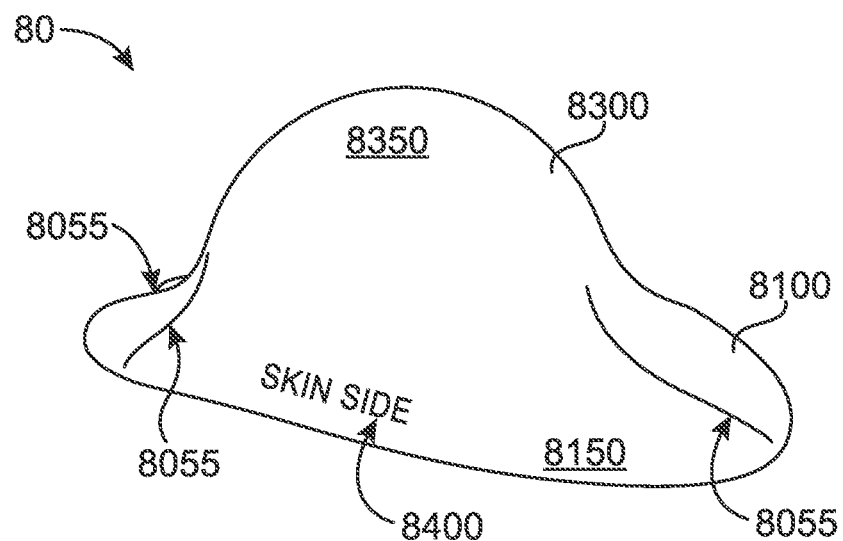
FIG. 12A shows a perspective view of another embodiment of a device according to the present technology.
Figure 12B:
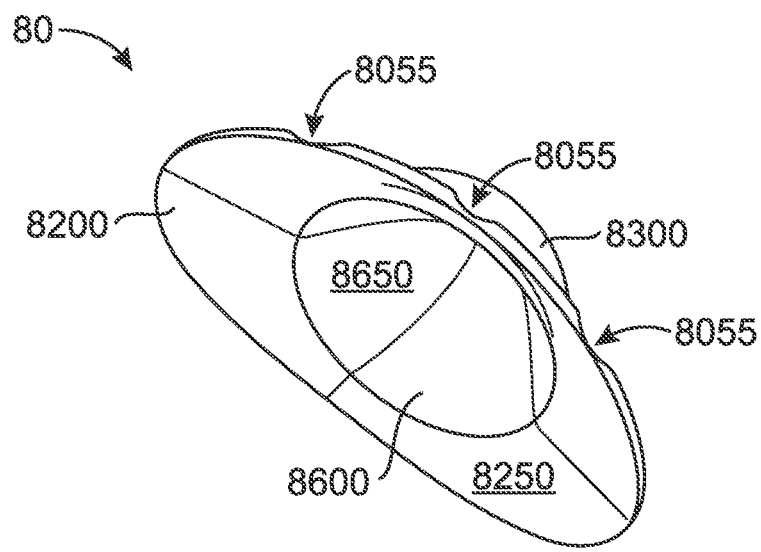
FIG. 12B shows another perspective view of the device of FIG. 12A.
Figure 12C:
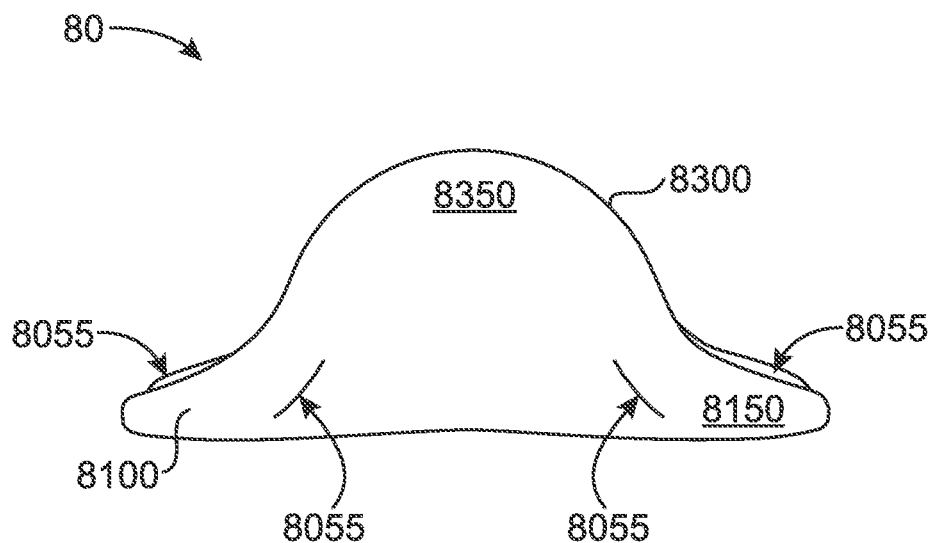
FIG. 12C shows a side perspective view of the device of FIGS. 12A-12B.
Figure 12D:
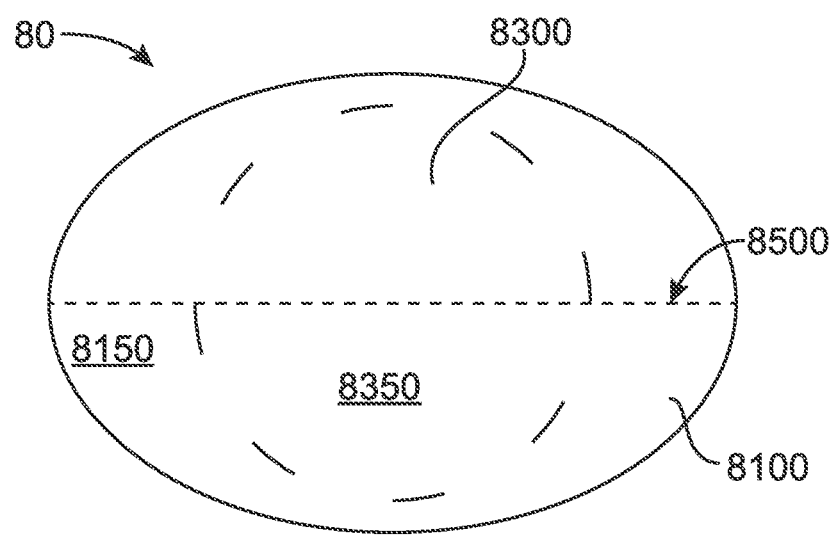
FIG. 12D shows a top view of the device of FIGS. 12A-12C.

In some embodiments, the top surface 8100 further includes one or more orientation markings 8500 for indicating to the subject how the device 80 should be oriented upon application. For example, as shown in FIG. 12D, the orientation markings 8500 may include a line indicating the midline of the device 80 which should be aligned parallel to the intergluteal cleft.

The contour portion 8300 of the top surface 8100 deviates from a plane (e.g., from a flat planar surface) with respect to the remaining portions of the top surface 8100, or deviates from the contour of the remaining portions of the top surface 8100. For example, as shown in FIG. 12A, the contour portion 8300 substantially protrudes from the top surface 8100. In some embodiments, such as that shown in FIG. 12A, the contour portion 8300 protrudes from the top surface 8100 to form a generally spheroid shape. In other embodiments, the contour portion 8300 forms a different shape, such as a disc, a mound, a cone, a teardrop, or a combination thereof. In other embodiments, the contour portion 8300 substantially recedes from the top surface 8100, for example to form a dent or divot in the top surface 8100. The contour portion 8300 includes a surface 8350 that may optionally include a texture similar to that described with respect to surface 8150 of the top surface 8100. In other embodiments, the surface 8350 does not include a texture, even in embodiments where surface 8150 includes a texture. In some embodiments, the contour portion 8300 is sized proportional to the subject's size (e.g., the subject's height, weight, BMI, waist circumference, etc.).

Figure 12E:
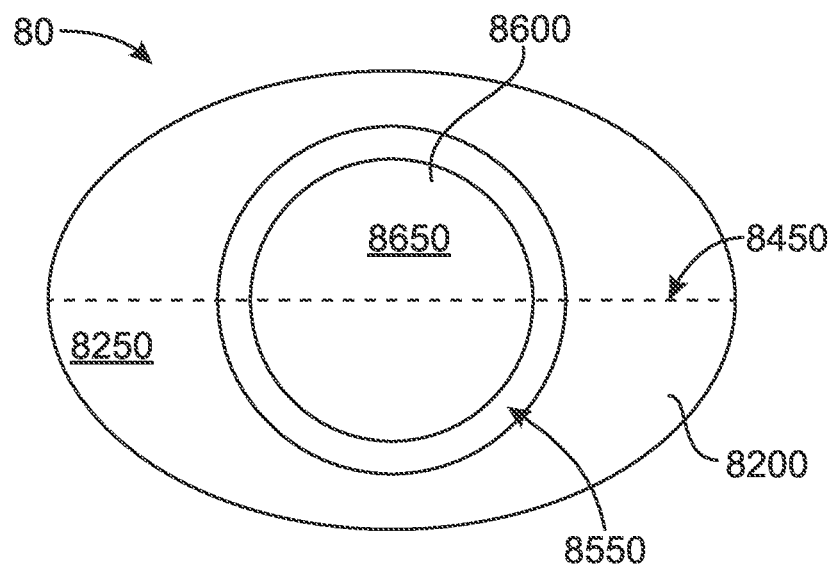
FIG. 12E shows a bottom view of the device of FIGS. 12A-12D.

The bottom surface 8200 of the device 80 may be formed of any durable material, optionally suitable for direct contact with skin, and which may allow the fluid to penetrate through the bottom surface 8200. In some such embodiments, the bottom surface 8200 comprises cotton. As shown in FIGS. 12B and 12E, the bottom surface 8200 of the device 80 includes a second surface 8250 which, in some embodiments, may include a coating (e.g., a waxy coating) to improve the integrity of the second layer 8200 to mechanical- or fluid-driven degradation. In such embodiments, the coating prevents fluid from penetrating from the interior of the device 80 through the bottom surface 8200 (e.g., trapping absorbed fluid within the device 80). In some embodiments, the second surface 8250 includes a texture. In some embodiments, the texture increases the adherence of the device 80 to the skin of the subject, for example to improve handling and manipulation of the device 80 during application and/or removal. In some embodiments, the texture includes one or more dimples.

The bottom surface 8200 may include a second contour portion 8600 which, in some embodiments, includes a contour that substantially deviates from a plane (e.g., from a planar surface defined at least in part by the remainder of the bottom surface 8200) or deviates from the contour of the remaining portions of the bottom surface 8200. For example, as shown in FIG. 12B, the second contour portion 8600 may recede from a planar surface defined by the remainder of the bottom surface 8200 such that an indentation is formed in the bottom surface 8200. The second contour portion 8600 includes a surface 8650 that may optionally include a texture, such as one or more dimples, to improve handling and manipulation of the device 80 during application and/or removal.

In some embodiments, the bottom surface 8200 further includes one or more informational markings 8450 for providing information to the subject. For example, the informational markings 8450 may indicate a midline of the device 80 and/or may indicate where the subject might apply pressure to properly install the device 80 in an intergluteal cleft.

In some embodiments, the bottom surface 8200 further includes one or more graphical indicators 8550 for indicating to the subject how the device 80 should be oriented upon application. For example, as shown in FIG. 12E, the orientation markings 8550 may indicate a central zone indicating the center of the device 80, which should ideally be aligned with the anus of the subject upon application.

The device 80 may additionally include an inner core 8700. Any remaining space between the top surface 8100 and the bottom surface 8200 may be filled by the inner core 8700. In such embodiments, the inner core 8700 may comprise an absorbent material such as cotton, located substantially within the contour portion 8300, 8600 of the device 80. The inner core 8700 may include an active agent such as a deodorant and/or an antibacterial agent.

In any embodiment disclosed herein, the inner core 8700 (also referred to as the third layer 8700 in various embodiments) may include a hygroscopic material, such as cotton or any other aqueous absorbent material or combination of materials. The inner core 8700 may include an active agent. In some embodiments, the active agent is a deodorant. In some embodiments, the active agent is an antibacterial agent. In some embodiments, the active agent is a hemorrhoid relief agent (e.g., disaccharide polysulfide). In some embodiments, the active agent is a numbing agent (e.g., a topical anesthetic such as benzocaine, butamben, dibucaine, lidocaine, oxybuprocaine, pramoxine, proparacaine, proxymetacaine, and tetracaine (alternatively referred to as amethocaine). In some embodiments, the active agent is two or more or three or more of: a deodorant, an antibacterial agent, a hemorrhoid relief agent, and a numbing agent. In some embodiments, the active agent comprises a deodorant, an antibacterial agent, a hemorrhoid relief agent and a numbing agent.

Figure 12F:
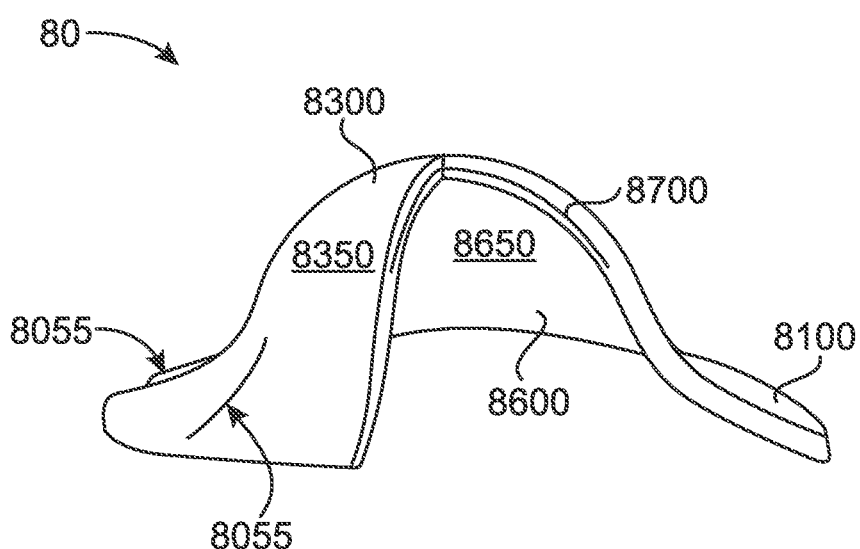
FIG. 12F shows a cross-sectional perspective view of the device of FIGS. 12A-12E.
Figure 13A:
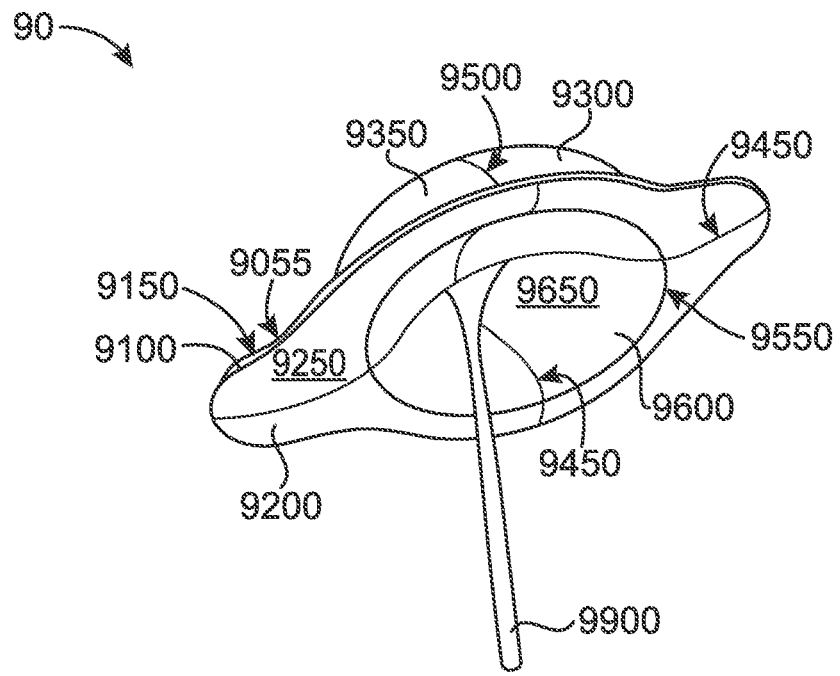
FIG. 13A shows a perspective view of another embodiment of a device according to the present technology.
Figure 13B:
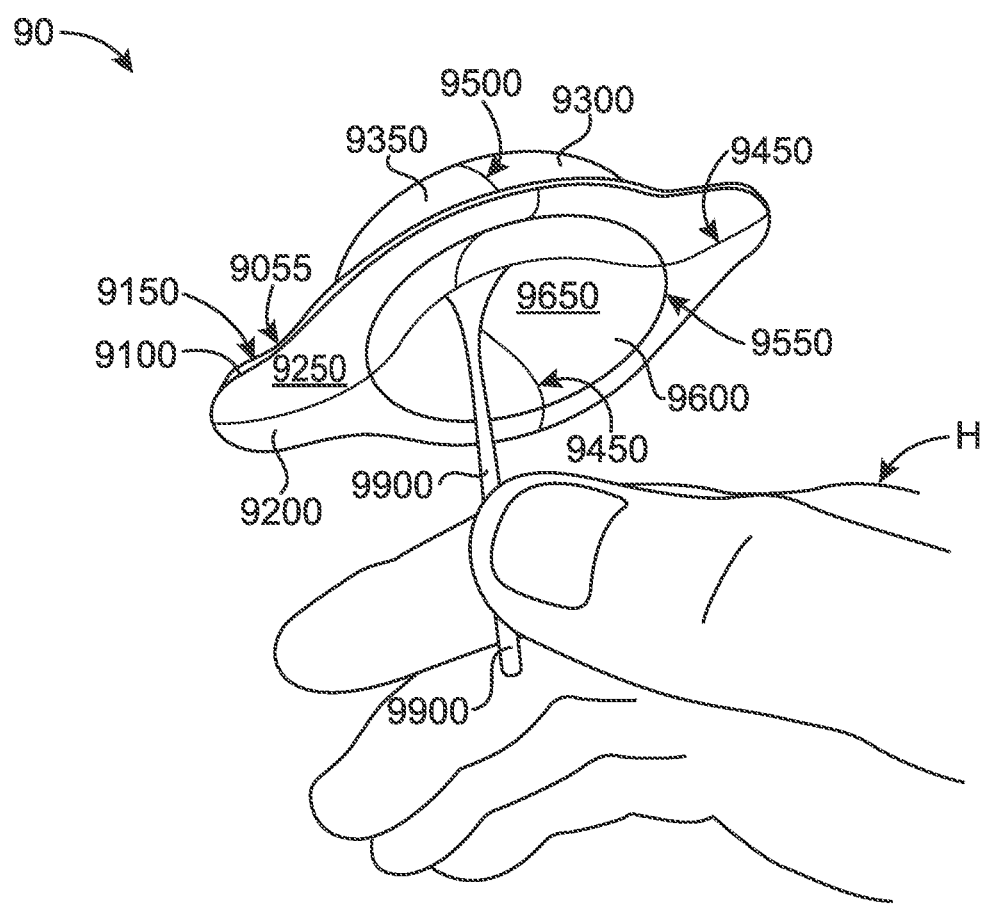
FIG. 13B shows a user grasping a removal tab of the device of FIG. 13A.
Figure 13C:
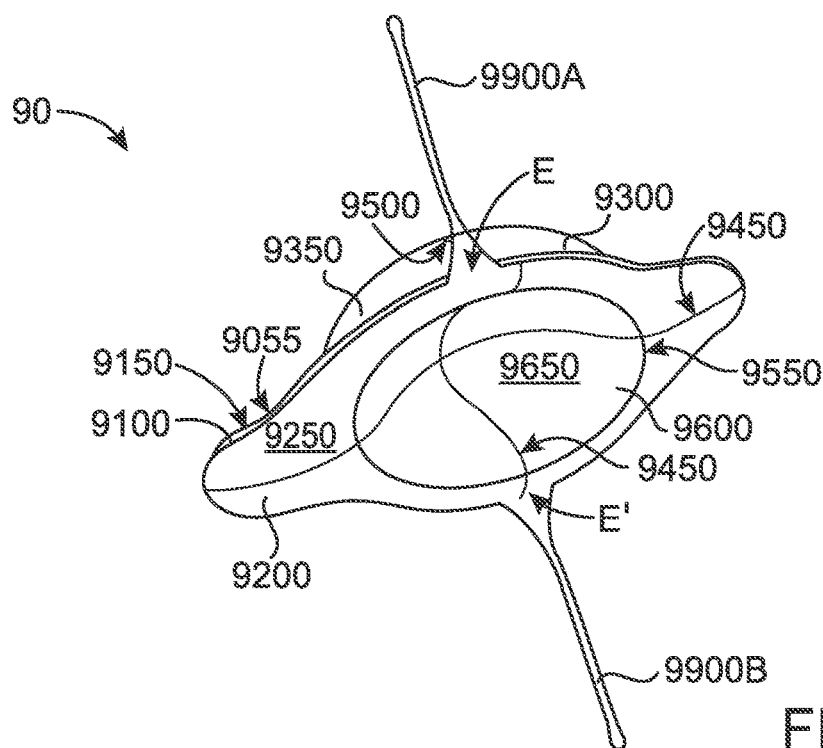
FIG. 13C shows a variation of the device of FIGS. 13A-13B having more than one removal tab.
Figure 13D:
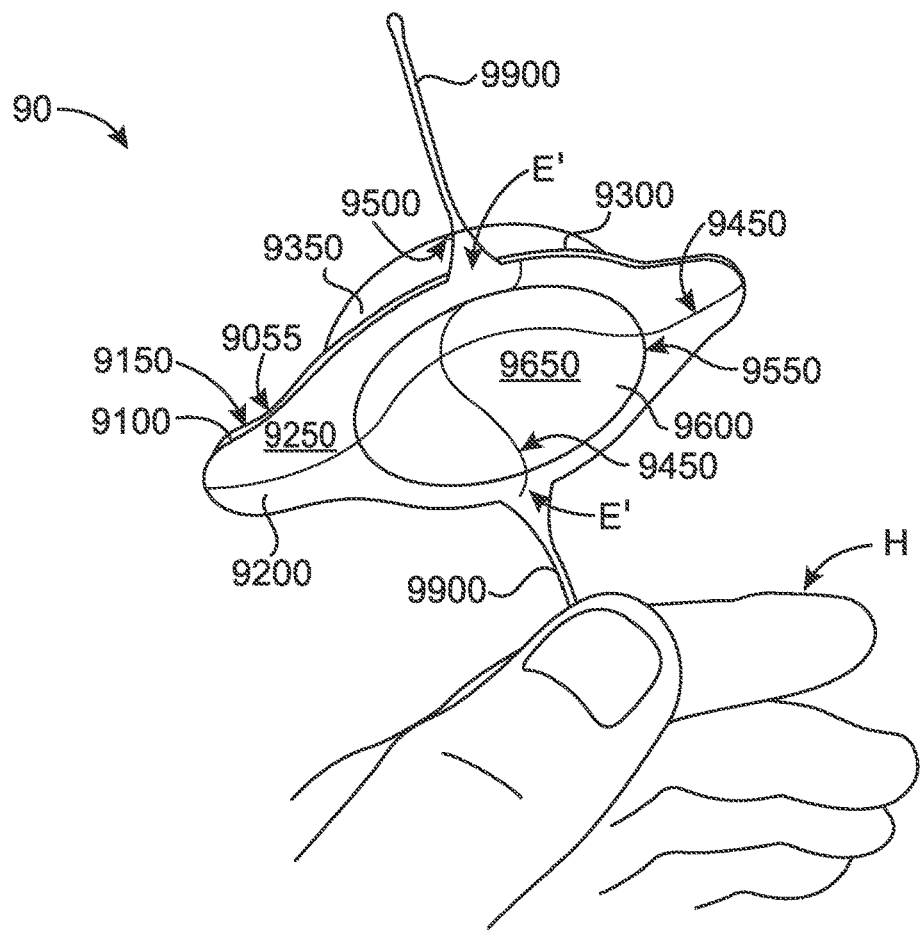
FIG. 13D shows a user grasping a removal tab of the device of FIG. 13B.

In some embodiments, the device 80 includes a cross-sectional shape defined by the top surface 8100, the bottom surface 8200, the inner core 8700, and the contour portions 8300, 8600. The cross-sectional shape may be chosen to enhance ease of use (e.g., installation and/or removal) of the device 80, subjects' comfort, etc. For example, as shown in FIG. 12F, the cross-sectional shape may be an arched dome-like shape having a substantially uniform thickness. For example and without limitation, the cross-sectional shape may alternatively include a circle, an oval, a rod, a rectangle, a square, a trapezoid, a rhombus, a parallelogram, a triangle, a hexagon, a pentagon, a heptagon, an octagon, a nonagon, a squircle, a portion of any of the forgoing (e.g., a semi-circle), a tapered configuration of any of the foregoing, or a combination of two or more of any of the foregoing (e.g., a cross-sectional profile including a quadrilateral portion and one or more protruding finger-like portion from one of the quadrilateral lengths and/or corners).

Any device disclosed herein may additionally include one or more creases. As used herein, the term "crease" refers to an indentation, fold, or overlapping region of the material. In some embodiments, a crease 8055 may include only a portion of the thickness of the material (e.g., a crease in only one layer of a multilayer device). In other embodiments, a crease may extend through the entire thickness of the device (e.g., through all layers of a multilayer device). In some embodiments, the creases enable the device to absorb substantially more fluid from skin of the subject than a comparably sized and shaped device that does not include creases, or alternatively includes fewer creases or creases of smaller dimension (e.g., length, width, volume and/or surface area).

In some embodiments, the creases are formed my converting (e.g., molding) a substantially flat piece of the sheet of material to form a contoured shaped, such as that generally shown in any one of FIGS. 1A-12F. For example, in the embodiment shown in FIGS. 12A-12F, the device 80 includes at least four creases 8055. In other embodiments, the device 80 includes at least two creases 8055, such as about three creases 8055, about four creases 8055, about five creases 8055, about six creases 8055, about seven creases 8055, about eight creases 8055, about nine creases 8055, about ten creases 8055, or more than about ten creases 8055.

Referring now generally to FIGS. 13A-13D, the present disclosure provides another embodiment of a device 90 for absorbing a fluid from skin of a subject. In such embodiments, the device 90 is formed of a substantially uniform sheet of material. The device 90 comprises a top surface 9100 which includes a contour portion 9300. The top surface 9100 may be formed of any material suitable for direct contact with skin and allows moisture to penetrate into the device 90. In some embodiments, the top surface 9100 comprises cotton. The top surface 9100 includes a surface (e.g., a body-facing surface) 9150. The surface 9150 may include a coating, such as a waxy coating, to prevent the top surface 9100 from adhering to the subject's skin too strongly. In some embodiments, the surface 9150 includes a texture. In some embodiments, the texture increases the adherence of the device 90 to the skin of the subject. In some embodiments, the texture includes one or more dimples.

In some embodiments, the top surface 9100 further includes one or more orientation markings 9500 for indicating to the subject how the device 90 should be oriented upon application. For example, the orientation markings 9500 may include a line indicating a midline of the device 90 which should be aligned parallel to or, as specifically shown in FIGS. 13A-13D, perpendicular to the intergluteal cleft.

The contour portion 9300 of the top surface 9100 deviates from a plane (e.g., from a flat planar surface) with respect to the remaining portions of the top surface 9100, or deviates from the contour of the remaining portions of the top surface 9100. For example, the contour portion 9300 may substantially protrude from the top surface 9100. In some embodiments, the contour portion 9300 protrudes from the top surface 9100 to form a generally spheroid shape. In other embodiments, the contour portion 9300 forms a different shape, such as a disc, a mound, a cone, a teardrop, or a combination thereof. In other embodiments, the contour portion 9300 substantially recedes from the top surface 9100, for example to form a dent or divot in the top surface 9100. The contour portion 9300 includes a surface 9350 that may optionally include a texture similar to that described with respect to surface 9150 of the top surface 9100. In other embodiments, the surface 9350 does not include a texture, even in embodiments where surface 9150 includes a texture. In some embodiments, the contour portion 9300 is sized proportional to the subject's size (e.g., the subject's height, weight, BMI, waist circumference, etc.).

The bottom surface 9200 of the device 90 may be formed of any durable material, optionally suitable for direct contact with skin, and which may allow the fluid to penetrate through the bottom surface 9200. In some such embodiments, the bottom surface 9200 comprises cotton. The bottom surface 9200 of the device 90 includes a second surface 9250 which, in some embodiments, may include a coating (e.g., a waxy coating) to improve the integrity of the second layer 9200 to mechanical- or fluid-driven degradation. In such embodiments, the coating prevents fluid from penetrating from the interior of the device 90 through the bottom surface 9200 (e.g., trapping absorbed fluid within the device 90). In some embodiments, the second surface 9250 includes a texture. In some embodiments, the texture increases the adherence of the device 90 to the skin of the subject, for example to improve handling and manipulation of the device 90 during application and/or removal. In some embodiments, the texture includes one or more dimples.

The bottom surface 9200 may include a second contour portion 9600 which, in some embodiments, includes a contour that substantially deviates from a plane (e.g., from a planar surface defined at least in part by the remainder of the bottom surface 9200) or deviates from the contour of the remaining portions of the bottom surface 9200. For example, the second contour portion 9600 may recede from a planar surface defined by the remainder of the bottom surface 9200 such that an indentation is formed in the bottom surface 9200. The second contour portion 9600 includes a surface 9650 that may optionally include a texture, such as one or more dimples, to improve handling and manipulation of the device 80 during application and/or removal.

The device 90 includes one or more removal tabs 9900, for example integrated with or attached to the bottom surface 9200. The one or more removal tabs 9900 enable the user to more easily remove the device 90 after use, for example when the device 90 has absorbed fluid. In some embodiments, shown representatively in FIG. 13A, the device 90 includes a single removal tab 9900 connected to the bottom surface 9200 at or near the center of the bottom surface 9200 (e.g., within the second contour portion 9600). To remove such an embodiment from an intergluteal cleft, the user grasps the removal tab 9900 with his or her hand H and pulls the removal tab 9900 in a direction generally away from the intergluteal cleft.

Alternatively, the device 90 may include more than one removal tab 9900, such as two removal tabs 9900. In such embodiments, the two removal tabs 9900 may be connected to the device 90 at any suitable location, preferably symmetrically opposed in relation to the center of the device 90. For example, as shown representatively in FIGS. 13C-13D, one removal tab 9900a may be attached to one edge E of the bottom surface 9200, while a second removal tab 9900b may be attached to a generally opposite edge E' of the bottom surface 9200. To remove such an embodiment from an intergluteal cleft, the user grasps the first removal tab 9900a, the second removal tab 9900b, or both removal tabs 9900a, 9900b with his or her hand H, and pulls in a direction generally away from the intergluteal cleft.

In some embodiments, the bottom surface 9200 further includes one or more informational markings 9450 for providing information to the subject. For example, the informational markings 9450 may indicate a midline of the device 90 and/or may indicate where the subject might apply pressure to properly install the device 90 in an intergluteal cleft.

In some embodiments, the bottom surface 9200 further includes one or more graphical indicators 9550 for indicating to the subject how the device 90 should be oriented upon application. For example, the orientation markings 9550 may indicate a central zone indicating the center of the device 90, which should ideally be aligned with the anus of the subject upon application.

The device 90 may additionally include other features described with respect to the embodiments shown in FIGS.

1-12F, such as an inner core identical to or similar to the inner core 8700 of device 80. As described with respect to device 80, the optional inner core of device 90 may include an active agent such as a deodorant, an antibacterial agent, a hemorrhoid relief agent, and/or a numbing agent. In some embodiments, the active agent is two or more or three or more of: a deodorant, an antibacterial agent, a hemorrhoid relief agent, and a numbing agent. In some embodiments, the active agent comprises a deodorant, an antibacterial agent, a hemorrhoid relief agent and a numbing agent.

In some embodiments, the device 90 includes a cross-sectional shape defined by the top surface 9100, the bottom surface 9200, the inner core 9700, and the contour portions 9300, 9600. The cross-sectional shape may be chosen to enhance ease of use (e.g., installation and/or removal) of the device 90, subjects' comfort, etc. For example, as shown in FIGS. 13A-13D, the cross-sectional shape may be an arched dome-like shape having a substantially uniform thickness. For example and without limitation, the cross-sectional shape may alternatively include a circle, an oval, a rod, a rectangle, a square, a trapezoid, a rhombus, a parallelogram, a triangle, a hexagon, a pentagon, a heptagon, an octagon, a nonagon, a squircle, a portion of any of the forgoing (e.g., a semi-circle), a tapered configuration of any of the foregoing, or a combination of two or more of any of the foregoing (e.g., a cross-sectional profile including a quadrilateral portion and one or more protruding finger-like portion from one of the quadrilateral lengths and/or corners).

Device 90 may also include one or more creases 9055, which may optionally include only a portion of the thickness of the material (e.g., a crease in only one layer of a multilayer device). In other embodiments, the one or more crease 9055 may extend through the entire thickness of the device 90. In some embodiments, the crease(s) 9055 enable the device 90 to absorb substantially more fluid from skin of the subject than a comparably sized and shaped device that does not include creases, or alternatively includes fewer creases or creases of smaller dimension (e.g., length, width, volume and/or surface area).

In some embodiments, the crease(s) 9055 are formed my converting (e.g., molding) a substantially flat piece of the sheet of material to form a contoured shaped, such as that generally shown in any one of FIGS. 13A-13D. The device 90 may include a single crease 9055, or alternatively may include at least two creases 9055, such as about three creases 9055, about four creases 9055, about five creases 9055, about six creases 9055, about seven creases 9055, about eight creases 9055, about nine creases 9055, about ten creases 9055, or more than about ten creases 9055.

In some embodiments, the present disclosure provides an absorbent device comprising a first layer including a body-facing surface containing an anti-stick material; a second layer disposed opposite the first body-facing surface; and a third layer disposed between the first and second layers and comprising an absorbent material. In some embodiments, at least a portion of the first layer includes a contour that substantially deviates from a plane. In some embodiments, the third layer further includes an inner core comprising a hygroscopic material. In some embodiments, the inner core is separated from the absorbent material by a barrier material. In some embodiments, the inner core further includes an active agent. In some embodiments, the active agent comprises a deodorant and/or an antibacterial agent. In some embodiments, the first layer includes a graphic element for providing application information to a user. In some embodiments, the second layer includes a graphic element for providing application information to a user. In some embodiments, the second layer includes a graphic element for providing application information to a user. In some embodiments, the body-facing surface includes a plurality of dimples. In some embodiments, the body-facing surface does not include an adhesive portion. In some embodiments, the contour that substantially deviates from a plane is spheroid.

In other embodiments, the present disclosure provides an absorbent device comprising a first, body-facing layer comprising a plurality of dimples; a second layer disposed opposite the first layer; and an inner core disposed between the first, body-facing layer and the second layer. In some embodiments, the first, body-facing layer does not include an adhesive portion. In some embodiments, the inner core layer comprises an absorbent material and optionally an active agent. In some embodiments, the absorbent material comprises cornstarch. In some embodiments, the active agent comprises a deodorant and/or antibacterial agent. In some embodiments, at least one of the first, body-facing layer and the second layer includes a graphic element for providing application information to a user.

2. Selected Embodiments of Methods of Treating or Preventing Perianal Sweating and/or Itching Devices disclosed herein may be used to absorb fluid (e.g., sweat, blood, feces, urine and/or pus) from skin (e.g., perianal skin) of a subject. In such embodiments, the method may include applying a device as diagnosed herein to the intergluteal cleft of a subject such that at least a portion of the device is in contact with skin proximal to the subject's anus (e.g., intergluteal skin).

In some embodiments, the present disclosure provides a method of absorbing a fluid proximal to an anus of a subject, the method comprising placing a device as disclosed herein at least partially within an intergluteal cleft of the subject. In some embodiments, the step of placing the device further includes placing the device in contact with perianal skin of the subject. In some embodiments, the method further comprises leaving the device in contact with skin of the subject for a period of time sufficient to absorb a fluid from the skin of the subject. In some embodiments, the fluid includes sweat, blood, feces, urine and/or pus. In some embodiments, the method further comprises removing the device after the period of time. In some embodiments, the device is removed within 24 hours of the step of placing the device within the intergluteal cleft.

Sweating and itching are common co-symptoms and, as such, methods of the present disclosure may simultaneously or substantially simultaneously absorb a fluid (e.g., sweat, blood, feces, urine and/or pus) from skin of the subject and reduce or eliminate itching proximal to the subject's anus. In other embodiments, the method reduces or eliminates itching without absorbing a fluid from skin proximal to the subject's anus, for example when the subject experiences itching but not fluid secretion. In any of these embodiments, the method comprises placing a device as disclosed herein at least partially within an intergluteal cleft of the subject. In some embodiments, the step of placing the device further includes placing the device in contact with perianal skin of the subject. In some embodiments, the method further comprises leaving the device in contact with skin of the subject for a period of time sufficient to reduce or eliminate the itching. In some embodiments, the method further comprises removing the device after the period of time. In some embodiments, the device is removed within 24 hours of the step of placing the device within the intergluteal cleft.

In some embodiments, the method of absorbing fluid proximal to the anus comprises placing the device at least partially within the intergluteal cleft of the subject before fluid is present near the anus (e.g., before onset of sweating and/or itching symptoms). In such embodiments, the fluid may be absorbed by the device to substantially or completely prevent sweating and/or itching symptoms.

In other embodiments, the present disclosure provides a method of preventing recurrence of itching in a subject. In such embodiments, the method comprises placing a device as disclosed herein at least partially within an intergluteal cleft of the subject. In some embodiments, the step of placing the device further includes placing the device in contact with perianal skin of the subject. In some embodiments, the method further comprises leaving the device in contact with skin of the subject for a period of time sufficient to reduce or eliminate the itching. In some embodiments, the method further comprises removing the device after the period of time. In some embodiments, the device is removed within 24 hours of the step of placing the device within the intergluteal cleft.

In any embodiments disclosed herein, the device may be inserted at least partially within the subject's intergluteal cleft and, after a period of time sufficient to absorb fluid from the intergluteal cleft, removed and discarded. If needed, a second, unused device as disclosed herein may be inserted at least partially within the subject's intergluteal cleft to absorb additional intergluteal fluid.

In some embodiments, the method further absorbs and/or neutralizes odors, for example by use of a device as disclosed herein that includes an antibacterial active agent.

In some embodiments, the method provides intergluteal fluid absorption sufficient to reduce, minimize, or prevent intergluteal fluid from contacting the subject's clothing (e.g., undergarment and/or outer wear).

In any embodiment disclosed herein, the fluid may comprise sweat.

In any embodiment disclosed herein, the fluid may consist essentially of sweat.

In any embodiment disclosed herein, the fluid may consist of sweat.

In some embodiments, the present disclosure provides a method of absorbing fluid (e.g., sweat) from an intergluteal cleft of a subject, the method comprising placing a device as disclosed herein at least partially within an intergluteal cleft of a subject. In some embodiments, the device is placed in contact with perianal tissue of the subject and/or in contact with a hemorrhoid of the subject.

3. Selected Embodiments of Devices for Treating or Preventing Hemorrhoids in a Subject In other embodiments, devices of the present disclosure treat or prevent hemorrhoids in a subject. In such embodiments, the device is configured to be placed, at least in part, in a subject's intergluteal cleft. In some embodiments, the device is configured to be placed in contact with a hemorrhoid to at least partially relieve a symptom of the hemorrhoid, such as itching, bleeding, burning, pain and/or swelling. In some embodiments, the device is configured to be placed in contact with a hemorrhoid to prevent progression (e.g., worsening) of the hemorrhoid. In other embodiments, the device is configured to be placed in contact with at least a portion of the subject's perianal tissue to prevent emergence of a hemorrhoid.

Referring now specifically to FIGS. 1A-1B and 2, a device 10 for treating or preventing hemorrhoids in a subject comprises a first layer 100 and a second layer 200 disposed opposite the first layer 100. At least a portion of the first layer 100 includes a contour 300 that deviates from a plane (e.g., from a flat planar surface).

The first layer 100 is oriented on the device 10 to be on contact with or adjacent to the subject. The first layer 100 may be formed of any material suitable for direct contact with skin and allows moisture to penetrate through the first layer 100. In some embodiments, the first layer 100 comprises cotton. The first layer 100 includes a surface (e.g., a body-facing surface) 150. The surface 150 may include a coating, such as a waxy coating, to prevent the first layer 100 from adhering to the subject's skin too strongly. In some embodiments, the surface 150 includes a texture. In some embodiments, the texture increases the adherence of the device 10 to the skin of the subject. In some embodiments, the texture includes one or more dimples.

In some embodiments, the first layer 100 further includes one or more informational markings 400 for providing information to the subject. For example, the informational markings 400 may indicate which side of the device 10 should be in contact with the subject's skin.

In some embodiments, the first layer 100 further includes one or more orientation markings 500 for indicating to the subject how the device 10 should be oriented upon application. For example, as shown in FIG. 1A, the orientation markings 500 may include a line indicating the midline of the device 10 which should be aligned parallel to the intergluteal cleft.

The contour portion 300 of the first layer 100 deviates from a plane (e.g., from a flat planar surface) with respect to the remaining portions of the first layer 100. For example, as shown in FIG. 1A, the contour portion 300 substantially protrudes from the first layer 100. In some embodiments, such as that shown in FIG. 1A, the contour portion 300 protrudes from the first layer 100 to form a generally spheroid shape. In other embodiments, the contour portion 300 forms a different shape or cross-sectional profile, such as a disc, a mound, a cone, a teardrop, a polygon, a quadrilateral (e.g., a rectangle, a square, a trapezoid, a rhombus, a parallelogram, etc.), a triangle, a hexagon, a pentagon, a heptagon, an octagon, a nonagon, a truncated polygon, a tapered configuration of any of the foregoing, or a combination thereof (e.g., a cross-sectional profile including a quadrilateral portion and one or more protruding finger-like portion from one of the quadrilateral lengths and/or corners). In other embodiments, the contour portion 300 substantially recedes from the first layer 100, for example to form a dent or divot in the first layer 100. The contour portion 300 includes a surface 350 that may optionally include a texture similar to that described with respect to surface 150 of the first layer 100. In other embodiments, the surface 350 does not include a texture, even in embodiments where surface 150 includes a texture. In some embodiments, the contour portion 300 is sized proportional to the subject's size (e.g., the subject's height, weight, BMI, waist circumference, etc.).

The second layer 200 of the device 10 may be formed of any durable material, optionally suitable for direct contact with skin, and which may allow moisture to penetrate through the second layer 200. In some embodiments, the second layer 200 comprises cotton. As shown in FIG. 1B, the second layer 200 of the device 10 includes a second surface 250 which, in some embodiments, may include a coating (e.g., a waxy coating) to improve the integrity of the second layer 200 to mechanical- or fluid-driven degradation. In some embodiments, the second surface 250 includes a texture. In some embodiments, the texture increases the adherence of the device 10 to the skin of the subject, for example to improve handling and manipulation of the device

10 during application. In some embodiments, the texture includes one or more dimples.

The second layer 200 may include a second contour portion 600 which, in some embodiments, includes a contour that substantially deviates from a plane (e.g., from a planar surface defined at least in part by the remainder of the second layer 200). For example, as shown in FIG. 1B, the second contour portion 600 may recede from a planar surface defined by the remainder of the second layer 200 such that an indentation is formed in the second layer 200. The second contour portion 600 includes a surface 650 that may optionally include a texture, such as one or more dimples, to improve handling and manipulation of the device 10 during application.

In some embodiments, the second layer 200 further includes one or more informational markings 450 for providing information to the subject. For example, the informational markings 450 may indicate where the subject might apply pressure to properly install the device 10 in an intergluteal cleft.

In some embodiments, the second layer 200 further includes one or more graphical indicators 550 for indicating to the subject how the device 10 should be oriented upon application. For example, as shown in FIG. 1B, the orientation markings 550 may indicate a central zone indicating the center of the device 10, which should ideally be aligned with the anus of the subject upon application.

The first layer 100 and the second layer 200 may be secured to each other around the periphery by any suitable means known to those of skill in the art. In one embodiment, shown in FIG. 1B, the first layer 100 and the second layer 200 are joined together by a seam or seal 255. In some embodiments, for example when the first layer 100 and/or the second layer 200 comprise cotton, the seam or seal 255 may be a physical joint (e.g., a sewn seam) or a chemical joint (e.g., an adhesive-enabled seal). In some embodiments, the first layer 100 and the second layer 200 are joined together by heat and/or compression.

In some embodiments, the device 10 includes a cross-sectional shape defined by the first layer 100, the second layer 200 and the contour 300. The cross-sectional shape may be chosen to enhance ease of use (e.g., installation and/or removal) of the device 10, subjects' comfort, etc. In some embodiments, the cross-sectional shape is substantially round, ovoid, rod-shaped, or polygonal. For example and without limitation, the cross-sectional shape may include a circle, an oval, a rod, a rectangle, a square, a trapezoid, a rhombus, a parallelogram, a triangle, a hexagon, a pentagon, a heptagon, an octagon, a nonagon, a squircle, a portion of any of the forgoing (e.g., a semi-circle), a tapered configuration of any of the foregoing, or a combination of two or more of any of the foregoing (e.g., a cross-sectional profile including a quadrilateral portion and one or more protruding finger-like portion from one of the quadrilateral lengths and/or corners).

As shown in FIG. 2, the embodiment of FIGS. 1A-1B includes a third layer 700 disposed between the first layer 100 and the second layer 200. The third layer 700 includes a filler material 750 for absorbing fluids and/or delivering an active agent to the subject upon application of the device 10 in the subject's intergluteal cleft. In some embodiments, the third layer 700 occupies the entire space between the first layer 100 and the second layer 200. In other embodiments, such as the one shown in FIG. 2, the filler material 750 comprises only a portion of the third layer 700 (e.g., occupies only a portion of the space between the first layer 100 and the second layer 200). In such embodiments, the remainder of the space between the first layer 100 and the second layer 200 not occupied by the filler material 750 may comprise a second filler material 800, which may be a relatively firm, structurally supportive material like cotton or a foam, for securing the filler material 750 in a desired location within the device 10. For example, as shown in FIG. 2, the third layer 700 may comprise an absorbent material 750 such as cotton, located substantially within the non-planar contour portion 300 of the first layer 100. To ensure the absorbent material 750 remains substantially in that location within the device 10, the third layer 700 further includes a second filler material 800 which is significantly more rigid than the absorbent material 750. In use, the more rigid second filler material 800 substantially prevents the absorbent material 750 from being forced out of its original location within the device 10 by, for example, physical forces exerted by a subject's gluteal muscles on the device 10.

In another embodiment, shown in FIGS. 3A-3B, a device 20 for treating or preventing hemorrhoids in a subject comprises a first layer 100 and a second layer 200 disposed opposite the first layer 100. At least a portion of the first layer 100 includes a contour 300 that deviates from a plane (e.g., from a flat planar surface).

General features of the first layer 100, the second layer 200, and the third layer 700 are substantially as described above with respect to FIGS. 1A-2.

A third layer 700 is disposed between the first layer 100 and the second layer 200, substantially in alignment with the contour portion 300 of the first layer 100. In some embodiments, the contour portion 300 of the first layer 100 is formed at least in part by the presence of the third layer 700 between the first layer 100 and the second layer 200.

In some embodiments, such as that shown in FIGS. 3A-3B, the third layer 700 comprises a shape that is substantially discoid. For example, the third layer 700 may be a round or circular pouch containing an absorbent material (as described above with respect to FIGS. 1A-2) that is secured between the first layer 100 and the second layer 200, causing the contour portion 300 of the first layer 100 to adopt a substantially discoid shape.

In another embodiment for treating or preventing hemorrhoids in a subject, shown in FIGS. 4-5, the first layer 100 and second layer 200 may be a continuous or semi-continuous form (e.g., without a flattened seam or seal 255 as shown in FIG. 1B) to form a device 30 having rounded edges. In such embodiments, the contour portion 300A may adopt any desired shape including, for example, a recessed cavity. The first layer 100, second layer 200, and/or the contour portion 300A may each include a surface 150, a surface 250 (not shown due to perspective) and/or a surface 350, respectively, as described above with respect to other embodiments. In some embodiments, the contour portion 300A is sized proportional to the subject's size (e.g., the subject's height, weight, BMI, waist circumference, etc.).

As shown in FIG. 5, the second layer 200 may include a contour portion 300B in addition to, or instead of, the contour portion 300A of the first layer 100. In embodiments including contour portions 300A/300B in both the first layer 100 and the second layer 200, respectively, the two contour portions 300A/300B may have an identical shape. In other embodiments (not shown), the two contour portions 300A/300B may have a substantially similar shape, or substantially different shapes. In some embodiments, the contour portion 300A/300B is sized proportional to the subject's size (e.g., the subject's height, weight, BMI, waist circumference, etc.).

The device 30 may include an inner core 700. Any remaining space between the first layer 100 and the second layer 200 may be filled with an absorbent filler material 800. In such embodiments, the absorbent filler material 800 acts to draw fluid into the device 30 through the first layer 100 and/or the second layer 200 and eventually to the inner core 700, for example along moisture paths 900.

In any embodiment disclosed herein, the inner core 700 (also referred to as the third layer 700 in various embodiments) may include a hygroscopic material 750, such as cotton or any other aqueous absorbent material or combination of materials. The inner core 700 may include an active agent 760. In some embodiments, the active agent 760 is a deodorant. In some embodiments, the active agent 760 is an antibacterial agent. In some embodiments, the active agent 760 is a hemorrhoid relief agent (e.g., disaccharide polysulfide). In some embodiments, the active agent 760 is a numbing agent (e.g., a topical anesthetic such as benzocaine, butamben, dibucaine, lidocaine, oxybuprocaine, pramoxine, proparacaine, proxymetacaine, and tetracaine (alternatively referred to as amethocaine). In some embodiments, the active agent is two or more or three or more of: a deodorant, an antibacterial agent, and a hemorrhoid relief agent. In some embodiments, the active agent comprises a deodorant, an antibacterial agent, a hemorrhoid relief agent and a numbing agent.

In another embodiment for treating or preventing hemorrhoids in a subject, shown in FIG. 6, a device 40 according to the present disclosure comprises a substantially bulbous head portion 42 and a substantially narrow tail portion 44. In such embodiments, the tail portion 44 enables safe and efficient handling of the device 40, for example between a subject's thumb and forefinger, while remaining discreet after application within the subject's intergluteal cleft.

The device 40 may include a first layer 100, a second layer 200, and a contour portion 300, similar to those shown and described above with respect to FIGS. 1A-5. General features of the first layer 100, the second layer 200, and the contour portion 300, including surfaces 150, 250 and 350, are substantially as described above with respect to other illustrated embodiments.

As shown in FIGS. 7A-7C, another embodiment of a device 50 for treating or preventing hemorrhoids in a subject includes a foldable crease 55 along a length of the device 50 for enabling efficient packaging of the device 50. In such embodiments, the device 50 includes a bifurcated first layer 100A/100B comprising an absorbent material and an optional coating (e.g., a waxy coating) suitable for direct contact with skin. Each of the bifurcated first layers 100A and 100B may include a surface 150A/150B. The surfaces 150A/150B may have properties similar to those described above with respect to surface 150 in other embodiments.

The device 50 also includes a bifurcated contour portion 300A/300B which, after folding is complete (e.g., as shown in FIG. 7C), has properties substantially similar to contour portion 300 in other embodiments described herein. More specifically, each of contour portions 300A/300B may have a surface 350A/350B that includes a texture, such as a plurality of dimples. In some embodiments, the bifurcated contour portion 300A/300B, after the device 50 is folded as shown in FIG. 7C, is sized proportional to the subject's size (e.g., the subject's height, weight, BMI, waist circumference, etc.).

When ready for use, the subject folds the device 50 along foldable crease 55 until the contour portion 300A is in contact with and/or continuous with the contour portion 300B, according to a progression shown in FIG. 7A to FIG. 7B to FIG. 7C. The resulting folded device 50 (FIG. 7C) is then inserted within the intergluteal cleft such that the contour portion 300A/300B is in contact with the perianal tissue and/or a hemorrhoid. When in position, the foldable crease 55 imparts a hinged outward force (e.g., a residual hinged spring force) which further enhances the stability of the device 50 in its installed position within the intergluteal cleft.

As shown in FIG. 8, the device 50 may include a bifurcated second layer 200A/200B disposed opposite the bifurcated first layer 100A/100B. The bifurcated second layer 200A/200B may be substantially the same as second layer 200 as described above with respect to other embodiments. For example, bifurcated second layer 200A may include a surface 250A, and bifurcated second layer 200B may include a surface 250B (not shown due to perspective) similar to or identical to second surface 250 described elsewhere in the present disclosure.

Similarly, the bifurcated contour portions 300A/300B may each include an inner core 700A/700B, which may each be substantially similar to inner core 700 described in connection with other embodiments disclosed herein. For example, inner core 700A/700B may include a hygroscopic material 750A/750B and optionally an active agent 760A/760B, all encapsulated in a permeable barrier layer 740A/740B. In some embodiments, an absorbent material 800A/800B is disposed between the permeable barrier layer 740A/740B and the first layer 100A/100B and optionally between the permeable barrier layer 740A/740B and the second layer 200A/200B.

An optional active agent 760A/760B may be included within the hygroscopic material 750A/750B. In some embodiments, active agent 760A is the same as the active agent 760B. In other embodiments, the active agent 760A is different than the active agent 760B.

In yet another embodiment for treating or preventing hemorrhoids in a subject, shown representatively in FIGS. 9-10, a device 60 according to the present disclosure comprises first layer 100 including a surface 150. The surface 150 includes at least one valley 152 and at least one plateau 154 for controlling flow of fluid into the device 60. In this embodiment, the device 60 also optionally includes a pair of adhesive areas 156 for providing additional adherence to the subject's skin upon application.

As shown in FIG. 10, the plateau portion(s) 154 may include a hydrophobic coating 158 which may attenuate the first layer 100 material's innate aqueous permeability properties. The valley(s) 152, in contrast, may not include the hydrophobic coating 158, enabling relatively easier permeability of aqueous fluids through the first layer 100 and/or the second layer 200 and into the third layer 700. In FIG. 10, this relative permeability difference between the plateau portions 154 and the valley portion(s) 152 is represented by moisture paths 900.

As in other embodiments, the third layer 700 may include a hygroscopic material 750 and optionally an active agent 760.

In yet another embodiment for treating or preventing hemorrhoids in a subject, shown representatively in FIG. 11, a device 70 according to the present technology comprises a first layer 100 and a second layer 200 disposed opposite the first layer 100. Each of the first layer 100 and the second layer 200 may include a surface 150 and a surface 250, respectively, which may have properties similar to those described above in connection with other disclosed embodiments.

The first layer 100 includes a contour portion 300A, which may additionally include one or more pillars 360A and one or more cavities 370A between the pillars 360A. Fluid absorbed by the contour portion 300A may thus cause the pillars 360A to expand radially, and the cavities 370A to shrink accordingly.

The second layer 200 includes a contour portion 300B, which may additionally include one or more pillars 360B and one or more cavities 370B between the pillars 360B. Fluid absorbed by the contour portion 300B may thus cause the pillars 360B to expand radially, and the cavities 370B to shrink accordingly.

In such embodiments, the first layer 100 and the second layer 200, and especially contour portions 300A/300B, may absorb substantial amounts of fluid without substantially expanding (e.g., without a diameter D of the combined contour portions 300A/300B substantially increasing). In some embodiments, the contour portion 300A/300B is sized proportional to the subject's size (e.g., the subject's height, weight, BMI, waist circumference, etc.).

Referring now generally to FIGS. 12A-12F, another embodiment of a device 80 for treating or preventing hemorrhoids in a subject is formed of a substantially uniform sheet of material. The device 80 comprises a top surface 8100 which includes a contour portion 8300. The top surface 8100 may be formed of any material suitable for direct contact with skin and allows moisture to penetrate into the device 80. In some embodiments, the top surface 8100 comprises cotton. The top surface 8100 includes a surface (e.g., a body-facing surface) 8150. The surface 8150 may include a coating, such as a waxy coating, to prevent the top surface 8100 from adhering to the subject's skin too strongly. In some embodiments, the surface 8150 includes a texture. In some embodiments, the texture increases the adherence of the device 80 to the skin of the subject. In some embodiments, the texture includes one or more dimples.

In some embodiments, the top surface 8100 further includes one or more informational markings 8400 for providing information to the subject. For example, the informational markings 8400 may indicate which side of the device 80 should be in contact with the subject's skin.

In some embodiments, the top surface 8100 further includes one or more orientation markings 8500 for indicating to the subject how the device 80 should be oriented upon application. For example, as shown in FIG. 12D, the orientation markings 8500 may include a line indicating the midline of the device 80 which should be aligned parallel to the intergluteal cleft.

The contour portion 8300 of the top surface 8100 deviates from a plane (e.g., from a flat planar surface) with respect to the remaining portions of the top surface 8100, or deviates from the contour of the remaining portions of the top surface 8100. For example, as shown in FIG. 12A, the contour portion 8300 substantially protrudes from the top surface 8100. In some embodiments, such as that shown in FIG. 12A, the contour portion 8300 protrudes from the top surface 8100 to form a generally spheroid shape. In other embodiments, the contour portion 8300 forms a different shape, such as a disc, a mound, a cone, a teardrop, or a combination thereof. In other embodiments, the contour portion 8300 substantially recedes from the top surface 8100, for example to form a dent or divot in the top surface 8100. The contour portion 8300 includes a surface 8350 that may optionally include a texture similar to that described with respect to surface 8150 of the top surface 8100. In other embodiments, the surface 8350 does not include a texture, even in embodiments where surface 8150 includes a texture.

In some embodiments, the contour portion 8300 is sized proportional to the subject's size (e.g., the subject's height, weight, BMI, waist circumference, etc.).

The bottom surface 8200 of the device 80 may be formed of any durable material, optionally suitable for direct contact with skin, and which may allow the fluid to penetrate through the bottom surface 8200. In some such embodiments, the bottom surface 8200 comprises cotton. As shown in FIGS. 12B and 12E, the bottom surface 8200 of the device 80 includes a second surface 8250 which, in some embodiments, may include a coating (e.g., a waxy coating) to improve the integrity of the second layer 8200 to mechanical- or fluid-driven degradation. In such embodiments, the coating prevents fluid from penetrating from the interior of the device 80 through the bottom surface 8200 (e.g., trapping absorbed fluid within the device 80). In some embodiments, the second surface 8250 includes a texture. In some embodiments, the texture increases the adherence of the device 80 to the skin of the subject, for example to improve handling and manipulation of the device 80 during application and/or removal. In some embodiments, the texture includes one or more dimples.

The bottom surface 8200 may include a second contour portion 8600 which, in some embodiments, includes a contour that substantially deviates from a plane (e.g., from a planar surface defined at least in part by the remainder of the bottom surface 8200) or deviates from the contour of the remaining portions of the bottom surface 8200. For example, as shown in FIG. 12B, the second contour portion 8600 may recede from a planar surface defined by the remainder of the bottom surface 8200 such that an indentation is formed in the bottom surface 8200. The second contour portion 8600 includes a surface 8650 that may optionally include a texture, such as one or more dimples, to improve handling and manipulation of the device 80 during application and/or removal.

In some embodiments, the bottom surface 8200 further includes one or more informational markings 8450 for providing information to the subject. For example, the informational markings 8450 may indicate a midline of the device 80 and/or may indicate where the subject might apply pressure to properly install the device 80 in an intergluteal cleft.

In some embodiments, the bottom surface 8200 further includes one or more graphical indicators 8550 for indicating to the subject how the device 80 should be oriented upon application. For example, as shown in FIG. 12E, the orientation markings 8550 may indicate a central zone indicating the center of the device 80, which should ideally be aligned with the anus of the subject upon application.

The device 80 may additionally include an inner core 8700. Any remaining space between the top surface 8100 and the bottom surface 8200 may be filled by the inner core 8700. In such embodiments, the inner core 8700 may comprise an absorbent material such as cotton, located substantially within the contour portion 8300, 8600 of the device 80. The inner core 8700 may include an active agent such as a deodorant and/or an antibacterial agent.

In any embodiment disclosed herein, the inner core 8700 (also referred to as the third layer 8700 in various embodiments) may include a hygroscopic material, such as cotton or any other aqueous absorbent material or combination of materials. The inner core 8700 may include an active agent. In some embodiments, the active agent is a deodorant. In some embodiments, the active agent is an antibacterial agent. In some embodiments, the active agent is a hemorrhoid relief agent (e.g., disaccharide polysulfide). In some embodiments, the active agent is a numbing agent (e.g., a topical anesthetic such as benzocaine, butamben, dibucaine, lidocaine, oxybuprocaine, pramoxine, proparacaine, proxymetacaine, and tetracaine (alternatively referred to as amethocaine). In some embodiments, the active agent is two or more or three or more of: a deodorant, an antibacterial agent, a hemorrhoid relief agent, and a numbing agent. In some embodiments, the active agent comprises a deodorant, an antibacterial agent, a hemorrhoid relief agent and a numbing agent.

In some embodiments, the device 80 includes a cross-sectional shape defined by the top surface 8100, the bottom surface 8200, the inner core 8700, and the contour portions 8300, 8600. The cross-sectional shape may be chosen to enhance ease of use (e.g., installation and/or removal) of the device 80, subjects' comfort, etc. For example, as shown in FIG. 12F, the cross-sectional shape may be an arched dome-like shape having a substantially uniform thickness. For example and without limitation, the cross-sectional shape may alternatively include a circle, an oval, a rod, a rectangle, a square, a trapezoid, a rhombus, a parallelogram, a triangle, a hexagon, a pentagon, a heptagon, an octagon, a nonagon, a squircle, a portion of any of the forgoing (e.g., a semi-circle), a tapered configuration of any of the foregoing, or a combination of two or more of any of the foregoing (e.g., a cross-sectional profile including a quadrilateral portion and one or more protruding finger-like portion from one of the quadrilateral lengths and/or corners).

Any device disclosed herein may additionally include one or more creases. As used herein, the term "crease" refers to an indentation, fold, or overlapping region of the material. In some embodiments, a crease 8055 may include only a portion of the thickness of the material (e.g., a crease in only one layer of a multilayer device). In other embodiments, a crease may extend through the entire thickness of the device (e.g., through all layers of a multilayer device). In some embodiments, the creases enable the device to absorb substantially more fluid from skin of the subject than a comparably sized and shaped device that does not include creases, or alternatively includes fewer creases or creases of smaller dimension (e.g., length, width, volume and/or surface area).

In some embodiments, the creases are formed my converting (e.g., molding) a substantially flat piece of the sheet of material to form a contoured shaped, such as that generally shown in any one of FIGS. 1A-12F. For example, in the embodiment shown in FIGS. 12A-12F, the device 80 includes at least four creases 8055. In other embodiments, the device 80 includes at least two creases 8055, such as about three creases 8055, about four creases 8055, about five creases 8055, about six creases 8055, about seven creases 8055, about eight creases 8055, about nine creases 8055, about ten creases 8055, or more than about ten creases 8055.

Referring now generally to FIGS. 13A-13D, the present disclosure provides another embodiment of a device 90 for absorbing a fluid from skin of a subject. In such embodiments, the device 90 is formed of a substantially uniform sheet of material. The device 90 comprises a top surface 9100 which includes a contour portion 9300. The top surface 9100 may be formed of any material suitable for direct contact with skin and allows moisture to penetrate into the device 90. In some embodiments, the top surface 9100 comprises cotton. The top surface 9100 includes a surface (e.g., a body-facing surface) 9150. The surface 9150 may include a coating, such as a waxy coating, to prevent the top surface 9100 from adhering to the subject's skin too strongly. In some embodiments, the surface 9150 includes a texture. In some embodiments, the texture increases the adherence of the device 90 to the skin of the subject. In some embodiments, the texture includes one or more dimples.

In some embodiments, the top surface 9100 further includes one or more orientation markings 9500 for indicating to the subject how the device 90 should be oriented upon application. For example, the orientation markings 9500 may include a line indicating a midline of the device 90 which should be aligned parallel to or, as specifically shown in FIGS. 13A-13D, perpendicular to the intergluteal cleft.

The contour portion 9300 of the top surface 9100 deviates from a plane (e.g., from a flat planar surface) with respect to the remaining portions of the top surface 9100, or deviates from the contour of the remaining portions of the top surface 9100. For example, the contour portion 9300 may substantially protrude from the top surface 9100. In some embodiments, the contour portion 9300 protrudes from the top surface 9100 to form a generally spheroid shape. In other embodiments, the contour portion 9300 forms a different shape, such as a disc, a mound, a cone, a teardrop, or a combination thereof. In other embodiments, the contour portion 9300 substantially recedes from the top surface 9100, for example to form a dent or divot in the top surface 9100. The contour portion 9300 includes a surface 9350 that may optionally include a texture similar to that described with respect to surface 9150 of the top surface 9100. In other embodiments, the surface 9350 does not include a texture, even in embodiments where surface 9150 includes a texture. In some embodiments, the contour portion 9300 is sized proportional to the subject's size (e.g., the subject's height, weight, BMI, waist circumference, etc.).

The bottom surface 9200 of the device 90 may be formed of any durable material, optionally suitable for direct contact with skin, and which may allow the fluid to penetrate through the bottom surface 9200. In some such embodiments, the bottom surface 9200 comprises cotton. The bottom surface 9200 of the device 90 includes a second surface 9250 which, in some embodiments, may include a coating (e.g., a waxy coating) to improve the integrity of the second layer 9200 to mechanical- or fluid-driven degradation. In such embodiments, the coating prevents fluid from penetrating from the interior of the device 90 through the bottom surface 9200 (e.g., trapping absorbed fluid within the device 90). In some embodiments, the second surface 9250 includes a texture. In some embodiments, the texture increases the adherence of the device 90 to the skin of the subject, for example to improve handling and manipulation of the device 90 during application and/or removal. In some embodiments, the texture includes one or more dimples.

The bottom surface 9200 may include a second contour portion 9600 which, in some embodiments, includes a contour that substantially deviates from a plane (e.g., from a planar surface defined at least in part by the remainder of the bottom surface 9200) or deviates from the contour of the remaining portions of the bottom surface 9200. For example, the second contour portion 9600 may recede from a planar surface defined by the remainder of the bottom surface 9200 such that an indentation is formed in the bottom surface 9200. The second contour portion 9600 includes a surface 9650 that may optionally include a texture, such as one or more dimples, to improve handling and manipulation of the device 80 during application and/or removal.

The device 90 includes one or more removal tabs 9900, for example integrated with or attached to the bottom surface 9200. The one or more removal tabs 9900 enable the user to more easily remove the device 90 after use, for example when the device 90 has absorbed fluid. In some embodiments, shown representatively in FIG. 13A, the device 90 includes a single removal tab 9900 connected to the bottom surface 9200 at or near the center of the bottom surface 9200 (e.g., within the second contour portion 9600). To remove such an embodiment from an intergluteal cleft, the user grasps the removal tab 9900 with his or her hand H and pulls the removal tab 9900 in a direction generally away from the intergluteal cleft.

Alternatively, the device 90 may include more than one removal tab 9900, such as two removal tabs 9900. In such embodiments, the two removal tabs 9900 may be connected to the device 90 at any suitable location, preferably symmetrically opposed in relation to the center of the device 90. For example, as shown representatively in FIGS. 13C-13D, one removal tab 9900a may be attached to one edge E of the bottom surface 9200, while a second removal tab 9900b may be attached to a generally opposite edge E' of the bottom surface 9200. To remove such an embodiment from an intergluteal cleft, the user grasps the first removal tab 9900a, the second removal tab 9900b, or both removal tabs 9900a, 9900b with his or her hand H, and pulls in a direction generally away from the intergluteal cleft.

In some embodiments, the bottom surface 9200 further includes one or more informational markings 9450 for providing information to the subject. For example, the informational markings 9450 may indicate a midline of the device 90 and/or may indicate where the subject might apply pressure to properly install the device 90 in an intergluteal cleft.

In some embodiments, the bottom surface 9200 further includes one or more graphical indicators 9550 for indicating to the subject how the device 90 should be oriented upon application. For example, the orientation markings 9550 may indicate a central zone indicating the center of the device 90, which should ideally be aligned with the anus of the subject upon application.

The device 90 may additionally include other features described with respect to the embodiments shown in FIGS. 1-12F, such as an inner core identical to or similar to the inner core 8700 of device 80. As described with respect to device 80, the optional inner core of device 90 may include an active agent such as a deodorant, an antibacterial agent, a hemorrhoid relief agent, and/or a numbing agent. In some embodiments, the active agent is two or more or three or more of: a deodorant, an antibacterial agent, a hemorrhoid relief agent, and a numbing agent. In some embodiments, the active agent comprises a deodorant, an antibacterial agent, a hemorrhoid relief agent and a numbing agent.

In some embodiments, the device 90 includes a cross-sectional shape defined by the top surface 9100, the bottom surface 9200, the inner core 9700, and the contour portions 9300, 9600. The cross-sectional shape may be chosen to enhance ease of use (e.g., installation and/or removal) of the device 90, subjects' comfort, etc. For example, as shown in FIGS. 13A-13D, the cross-sectional shape may be an arched dome-like shape having a substantially uniform thickness. For example and without limitation, the cross-sectional shape may alternatively include a circle, an oval, a rod, a rectangle, a square, a trapezoid, a rhombus, a parallelogram, a triangle, a hexagon, a pentagon, a heptagon, an octagon, a nonagon, a squircle, a portion of any of the forgoing (e.g., a semi-circle), a tapered configuration of any of the foregoing, or a combination of two or more of any of the foregoing (e.g., a cross-sectional profile including a quadrilateral portion and one or more protruding finger-like portion from one of the quadrilateral lengths and/or corners).

Device 90 may also include one or more creases 9055, which may optionally include only a portion of the thickness of the material (e.g., a crease in only one layer of a multilayer device). In other embodiments, the one or more crease 9055 may extend through the entire thickness of the device 90. In some embodiments, the crease(s) 9055 enable the device 90 to absorb substantially more fluid from skin of the subject than a comparably sized and shaped device that does not include creases, or alternatively includes fewer creases or creases of smaller dimension (e.g., length, width, volume and/or surface area).

In some embodiments, the crease(s) 9055 are formed my converting (e.g., molding) a substantially flat piece of the sheet of material to form a contoured shaped, such as that generally shown in any one of FIGS. 13A-13D. The device 90 may include a single crease 9055, or alternatively may include at least two creases 9055, such as about three creases 9055, about four creases 9055, about five creases 9055, about six creases 9055, about seven creases 9055, about eight creases 9055, about nine creases 9055, about ten creases 9055, or more than about ten creases 9055.

In some embodiments, the present disclosure provides an absorbent device comprising a first layer including a body-facing surface containing an anti-stick material; a second layer disposed opposite the first body-facing surface; and a third layer disposed between the first and second layers and comprising an absorbent material. In some embodiments, at least a portion of the first layer includes a contour that substantially deviates from a plane. In some embodiments, the third layer further includes an inner core comprising a hygroscopic material. In some embodiments, the inner core is separated from the absorbent material by a barrier material. In some embodiments, the inner core further includes an active agent. In some embodiments, the active agent comprises one or more of: a deodorant, an antibacterial agent, and a hemorrhoid relief agent. In some embodiments, the first layer includes a graphic element for providing application information to a user. In some embodiments, the second layer includes a graphic element for providing application information to a user. In some embodiments, the second layer includes a graphic element for providing application information to a user. In some embodiments, the body-facing surface includes a plurality of dimples. In some embodiments, the body-facing surface does not include an adhesive portion. In some embodiments, the contour that substantially deviates from a plane is spheroid.

In other embodiments, the present disclosure provides an absorbent device comprising a first, body-facing layer comprising a plurality of dimples; a second layer disposed opposite the first layer; and an inner core disposed between the first, body-facing layer and the second layer. In some embodiments, the first, body-facing layer does not include an adhesive portion. In some embodiments, the inner core layer comprises an absorbent material and optionally an active agent. In some embodiments, the absorbent material comprises cornstarch. In some embodiments, the active agent comprises one or more of: a deodorant, an antibacterial agent, and a hemorrhoid relief agent. In some embodiments, at least one of the first, body-facing layer and the second layer includes a graphic element for providing application information to a user.

4. Selected Embodiments of Methods of Treating or Preventing Hemorrhoids in a Subject Devices disclosed herein may be used to treat or prevent a hemorrhoid in a subject. In such embodiments, the method may include applying a device as diagnosed herein to the intergluteal cleft of a subject such that at least a portion of the device is in contact with the hemorrhoid.

In some embodiments, the method comprises placing the device at least partially within the intergluteal cleft of the subject before a hemorrhoid develops (e.g., before onset of hemorrhoid-related pain and/or itching symptoms). In some embodiments, the subject is at increased risk of developing hemorrhoids. In some embodiments, the subject has one or more hemorrhoid risk factors: constipation, low fiber diet, high fat diet, obesity, sedentary lifestyle, dehydration, alcoholism, pregnancy, recent childbirth, diarrhea, damage or atrophy of pelvic floor muscle (e.g., from recent surgery, pregnancy or childbirth), heart disease, liver disease, age of 50 years or older, and/or family history of hemorrhoids.

In other embodiments, the method comprises providing a device as disclosed herein to a subject in need of treatment or prevention of hemorrhoids, and instructing the subject to insert the device at least partially within the intergluteal cleft.

In some embodiments, the method results in an attenuation of one or more symptoms associated with the hemorrhoid, such as pain, itching, and/or swelling.

In some embodiments, the method results in a downgrade of the hemorrhoid grade. For example, a grade 3 hemorrhoid of a subject may, after treatment according to the present disclosure, be reduced to a grade 2 hemorrhoid.

In other embodiments, the method results in a delay (e.g., a substantial delay) in the need for a clinical procedure to remove the hemorrhoid. In some embodiments, the clinical procedure is selected from the group consisting of: rubber band ligation, sclerotherapy, cauterization, hemorrhoidectomy, hemorrhoidal dearterialization, and stapled hemorrhoidopexy.

In yet other embodiments, a method of treating a hemorrhoid as disclosed herein further excludes a clinical intervention to treat the hemorrhoid. In some embodiments, the clinical intervention is selected from the group consisting of: rubber band ligation, sclerotherapy, cauterization, hemorrhoidectomy, hemorrhoidal dearterialization, and stapled hemorrhoidopexy.

In some embodiments, the present disclosure provides a method of treating or preventing a hemorrhoid in a subject, the method comprising placing a device as disclosed herein at least partially within an intergluteal cleft of a subject. In some embodiments, the device is placed in contact with a hemorrhoid of the subject and/or in contact with perianal tissue of the subject. In some embodiments, the device includes a numbing agent (e.g., a topical anesthetic such as benzocaine, butamben, dibucaine, lidocaine, oxybuprocaine, pramoxine, proparacaine, proxymetacaine, and tetracaine (alternatively referred to as amethocaine)).

As one of skill in the art will recognize, other indications include similar symptoms to those of a hemorrhoid, and are even confused with a hemorrhoid diagnosis. Accordingly, any method disclosed herein may also be used to treat and/or prevent one or more symptoms associated with a disorder other than hemorrhoids. In some embodiments, the disorder is one or more of: fissures, fistulae, abscesses, colorectal cancer, rectal varices, itching, rectal bleeding, colitis, inflammatory bowel disease, diverticular disease, and angiodysplasia.

EXAMPLES

Example 1. An absorbent device comprising a first layer including a body-facing surface containing an anti-stick material; a second layer disposed opposite the first body-facing surface; and a third layer disposed between the first and second layers and comprising an absorbent material, wherein at least a portion of the first layer includes a contour that substantially deviates from a plane.

Example 2. The device of Example 1, wherein the third layer further includes an inner core comprising a hygroscopic material.

Example 3. The device of Example 2, wherein the inner core is separated from the absorbent material by a barrier material.

Example 4. The device of Example 1, wherein the inner core further includes an active agent.

Example 5. The device of Example 4, wherein the active agent comprises one or more of: a deodorant, an antibacterial agent, a hemorrhoid relief agent, and a numbing agent.

Example 6. The device of Example 1, wherein the first layer includes a graphic element for providing application information to a user.

Example 7. The device of Example 1, wherein the second layer includes a graphic element for providing application information to a user.

Example 8. The device of Example 6, wherein the second layer includes a graphic element for providing application information to a user.

Example 9. The device of Example 1, wherein the body-facing surface includes a plurality of dimples.

Example 10. The device of Example 1, wherein the body-facing surface does not include an adhesive portion.

Example 11. The device of Example 1, wherein the contour that substantially deviates from a plane is spheroid.

Example 12. The device of Example 1, wherein the second layer further comprises one or more removal tabs.

Example 13. The device of Example 1, wherein the first layer further comprises one or more creases.

Example 14. An absorbent device comprising a first, body-facing layer comprising a plurality of dimples; a second layer disposed opposite the first layer; and an inner core disposed between the first, body-facing layer and the second layer.

Example 15. The device of Example 14, wherein the first, body-facing layer does not include an adhesive portion.

Example 16. The device of Example 14, wherein the inner core layer comprises an absorbent material and optionally an active agent.

Example 17. The device of Example 16, wherein the absorbent material comprises cornstarch.

Example 18. The device of Example 16, wherein the active agent comprises one or more of: a deodorant, an antibacterial agent, a hemorrhoid relief agent, and a numbing agent.

Example 19. The device of Example 14, wherein at least one of the first, body-facing layer and the second layer includes a graphic element for providing application information to a user.

Example 20. The device of Example 14, wherein the second layer further comprises one or more removal tabs.

Example 21. The device of Example 14, wherein the first layer further comprises one or more creases.

Example 22. A method of treating or preventing a hemorrhoid in a subject, the method comprising:
Example placing a device according to Example 1 at least partially within an intergluteal cleft of a subject.

Example 23. The method of Example 22, wherein the step of placing the device further includes placing the device in contact with a hemorrhoid of the subject and/or in contact with perianal tissue of the subject.

Example 24. A method of treating or preventing a hemorrhoid in a subject, the method comprising placing a device according to Example 14 at least partially within an intergluteal cleft of a subject.

Example 25. The method of Example 24, wherein the step of placing the device further includes placing the device in contact with a hemorrhoid of the subject and/or in contact with perianal tissue of the subject.

Example 26. A method of absorbing a fluid proximal to an anus of a subject, the method comprising placing a device according to Example 1 at least partially within an intergluteal cleft of a subject.

Example 27. The method of Example 26, wherein the step of placing the device further includes placing the device in contact with perianal skin of the subject.

Example 28. A method of absorbing a fluid proximal to an anus of a subject, the method comprising placing a device according to Example 14 at least partially within an intergluteal cleft of a subject.

Example 29. The method of Example 28, wherein the step of placing the device further includes placing the device in contact with perianal skin of the subject.

Example 30. A method of preventing, reducing or eliminating itching proximal to an anus of a subject, the method comprising placing a device according to Example 1 at least partially within an intergluteal cleft of a subject.

Example 31. The method of Example 30, wherein the step of placing the device further includes placing the device in contact with perianal skin of the subject.

Example 32. A method of preventing, reducing or eliminating itching proximal to an anus of a subject, the method comprising placing a device according to Example 14 at least partially within an intergluteal cleft of a subject.

Example 33. The method of Example 32, wherein the step of placing the device further includes placing the device in contact with perianal skin of the subject.

CONCLUSION

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments.

From the foregoing, it will be appreciated that specific embodiments of the invention have been described herein for purposes of illustration, but well-known structures and functions have not been shown or described in detail to avoid unnecessarily obscuring the description of the embodiments of the technology. Where the context permits, singular or plural terms may also include the plural or singular term, respectively.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to". Words using the singular or plural number also include the plural and singular number, respectively. Additionally, the words "herein," "above," and "below" and words of similar import, when used in this application, shall refer to this application as a whole and not to any particular portions of the application.

The term "treatment" in relation a given disease or disorder, includes, but is not limited to, inhibiting the disease or disorder, for example, arresting the development of the disease or disorder; relieving the disease or disorder, for example, causing regression of the disease or disorder; or relieving a condition caused by or resulting from the disease or disorder, for example, relieving, preventing or treating symptoms of the disease or disorder. The term "prevention" in relation to a given disease or disorder means: preventing the onset of disease development if none had occurred, preventing the disease or disorder from occurring in a subject that may be predisposed to the disorder or disease but has not yet been diagnosed as having the disorder or disease, and/or preventing further disease/disorder development if already present.

The description of embodiments of the disclosure is not intended to be exhaustive or to limit the disclosure to the precise form disclosed. While the specific embodiments of, and examples for, the disclosure are described herein for illustrative purposes, various equivalent modifications are possible within the scope of the disclosure, as those skilled in the relevant art will recognize.

Specific elements of any foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

From the foregoing, it will be appreciated that specific embodiments of the invention have been described herein for purposes of illustration, but that various modifications may be made without deviating from the scope of the invention. Accordingly, the invention is not limited except as by the appended claims.

What is claimed is:

1. A method of absorbing sweat proximal to the anus of a subject, the method comprising:
    inserting a device in an intergluteal cleft of a subject, the device consisting essentially of:
        a sheet of material having a substantially uniform thickness throughout, and comprising:
            a first, generally planar portion comprising at least one crease;

a second generally dome-shaped portion that protrudes from the first generally planar portion and is surrounded by the first, generally planar portion, and is sized and shaped to be placed in an intergluteal cleft and proximal to the anus of the subject; and a body-facing surface including:
a texture configured to increase adherence of the device to skin of the subject, and
a hydrophobic coating.

2. The method of claim 1, wherein the sheet of material includes a plurality of layers, and wherein the plurality of layers are secured to each other by a compression seal.

3. The method of claim 1, wherein the hydrophobic coating is disposed on only a portion of the body-facing surface.

4. The method of claim 1, wherein the sheet of material does not include cotton.

5. The method of claim 1, wherein the sheet of material does not include an adhesive for increasing adherence of the device to skin of the subject.

6. A method of absorbing sweat proximal to the anus of a subject, the method comprising:

inserting a device in an intergluteal cleft of a subject, the device consisting essentially of:
a creased multilayer sheet of material having a substantially uniform thickness throughout, and comprising:
a first portion surrounding a second portion that protrudes from the first portion;
a first, body-facing layer including a surface including a hydrophobic coating configured to attenuate adherence of the first-body-facing layer to skin proximal to the anus of the subject;
a second layer disposed opposite the first, body-facing layer; and
no adhesive for increasing adherence of the device to skin of the subject.

7. The method of claim 6, wherein the second layer does not include an adhesive for increasing adherence of the device to skin of the subject.

8. The method of claim 6, wherein the first, body-facing layer includes a texture configured to increase adherence of the device to skin proximal to the anus of the subject.

9. The method of claim 6, wherein the first, body-facing layer and the second layer are joined together by a seal.

10. The method of claim 6, wherein the seal is a compression seal.

11. The method of claim 6, wherein the compression seal does not include a chemical or adhesive.

12. The method of claim 6, wherein the second portion protrudes from the first generally planar portion in an arched dome-like shape.

13. A method of absorbing sweat proximal to the anus of a subject, the method comprising:

inserting a device in an intergluteal cleft of a subject, the device consisting essentially of:
a first, dome-shaped portion having a first thickness and comprising:
a body-facing surface, and
a hydrophobic coating disposed on at least a portion of the body-facing surface;
a second portion substantially surrounding the first, dome-shaped portion and having a second thickness substantially the same as the first thickness; and
at least one crease disposed through at least a portion of at least one of the first thickness and the second thickness,
wherein the device is sized and shaped to be placed proximal to the anus of the subject.

14. The method of claim 13, wherein the first, dome-shaped portion and the second portion are formed from a plurality of layers of material.

15. The method of claim 13, wherein the device does not include cotton.

16. The method of claim 13, wherein the first, body-facing layer does not include an adhesive for increasing adherence of the device to skin of the subject.

* * * * *